Figure 1:
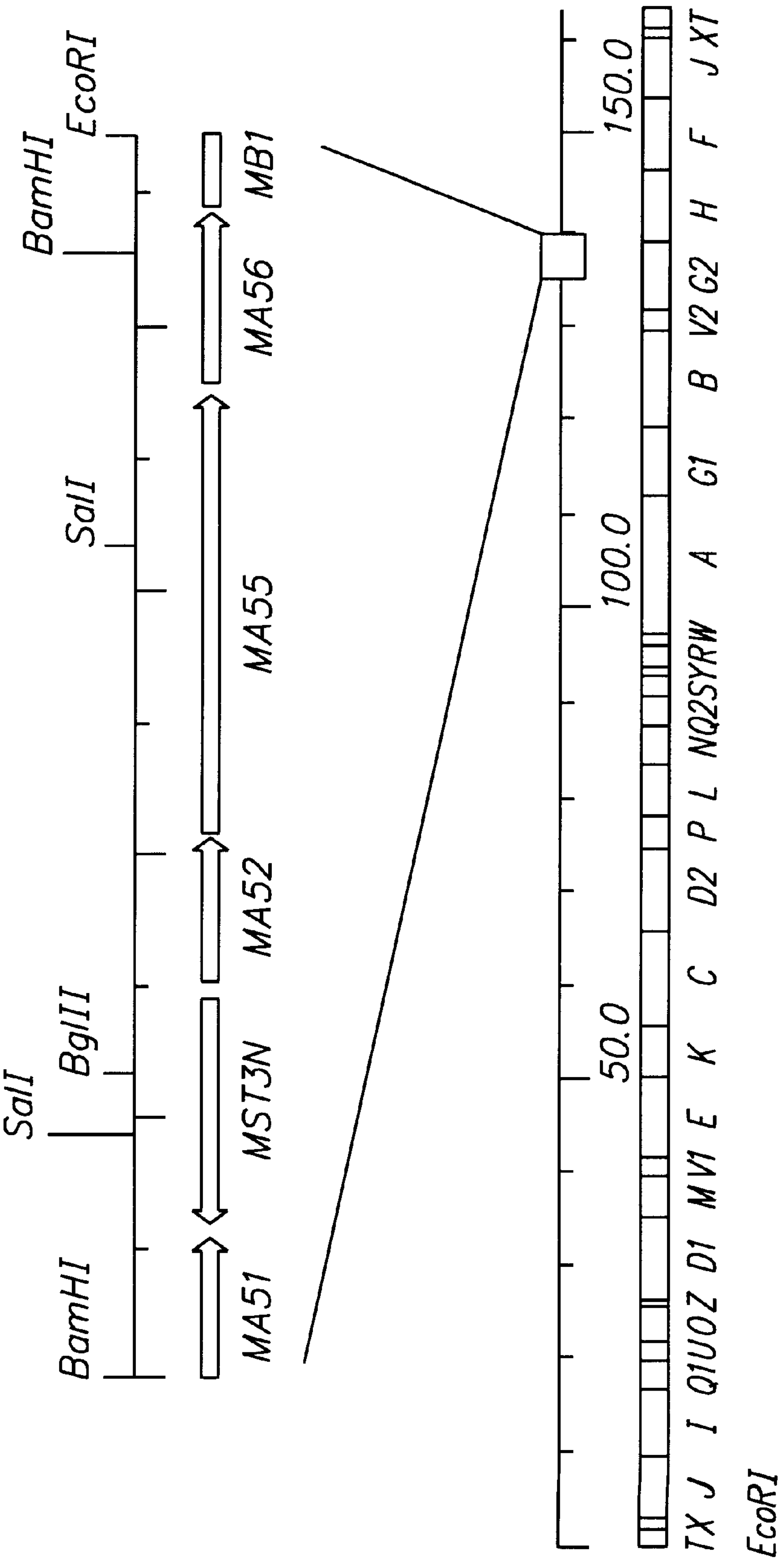

US006136579A

United States Patent [19]

Jackson

[11] Patent Number: 6,136,579

[45] Date of Patent: Oct. 24, 2000

[54] METHOD OF PRODUCING α2,3-SIALYLTRANSFERASE

[75] Inventor: Ronald James Jackson, Evatt, Australia

[73] Assignee: Commonwealth Scientific and Industrial Research Organization, Australia

[21] Appl. No.: 09/068,655

[22] PCT Filed: Nov. 15, 1996

[86] PCT No.: PCT/AU96/00725

§ 371 Date: Aug. 31, 1998

§ 102(e) Date: Aug. 31, 1998

[87] PCT Pub. No.: WO97/18302

PCT Pub. Date: May 22, 1997

[30] Foreign Application Priority Data

Nov. 15, 1995 [AU] Australia .............................. PN 6587

[51] Int. Cl.[7] ................................ C12N 9/10; C08B 3/06

[52] U.S. Cl. .......................... 435/193; 435/183; 536/69.1

[58] Field of Search .................................... 435/193, 183; 536/23.2

[56] References Cited

U.S. PATENT DOCUMENTS

| | | | |
|---|---|---|---|
| 4,727,136 | 2/1988 | Jennings et al. . | |
| 5,017,487 | 5/1991 | Stunnenberg et al. | 435/235 |
| 5,079,353 | 1/1992 | Ratcliffe et al. . | |
| 5,352,670 | 10/1994 | Venot et al. . | |
| 5,374,655 | 12/1994 | Kashem et al. . | |
| 5,384,249 | 1/1995 | Sasaki et al. | 435/68.1 |
| 5,461,143 | 10/1995 | Wong et al. . | |

FOREIGN PATENT DOCUMENTS

| | | |
|---|---|---|
| 0 475 354 | 3/1992 | European Pat. Off. . |
| 93/18157 | 9/1993 | WIPO . |
| 95/04816 | 2/1995 | WIPO . |
| 96/32491 | 10/1996 | WIPO . |
| 97/18302 | 5/1997 | WIPO . |

OTHER PUBLICATIONS

Gillespie W. et al., (1992) "Cloning and Expression of the Galβ1,3 GalNAc α2,3 sialyltransferase" *J. Biol. Chem.* 267(29):21004–21010.

Sasaki et al., (1993) "Expression Cloning of a novel Galβ(1–3/1–4) GlcNac α2,3–sialyltransferase using lectin resistance selection" *J. Biol. Chem.* 268(30):22782–22787.

Lee Y–C et al. (1994) "Cloning and Expression of cDNA for a new type of Galβ 1,3 GalNAc α2,3 sialyltransferase", *J. Biol. Chem.* 269(13):10028–10033.

Goebel S.J. et al., (1990), "The complete DNA sequence of Vaccinia virus" *Virology* 179(1):247–266.

Palcic (1994) Methods in Enzymology 230:300–316.

Weinstein et al., "Purification of a Galβ1→4GlcNAc α2→6 Sialyltransferase and a Galβ1→3(4)GlcNAc α2→3 Sialyltransferase to Homogeneity from Rat Liver" *J. Biol. Chem.*, 257(22):13835–13844 (1982).

Esposito (1991) "Properties of the Virus Particle", *Archives of Virology* (Suppl) 2:91–102.

Gross et al. (1990) "A highly sensitive fluorometric assay for sialyltransferase activity using CMP–9–fluoresceinyl–NeuAc as donor" *Analytical Biochem* 186:127–134.

McFadden G. (1988) "Poxviruses of Rabbits" In "Virus Diseases in laboratory and captive animals" Ed. G. Darai, Martinus Nijhoff Publishers Boston 36–62.

Russell, J. R. and Robbins, S.J. (1989) "Cloning and Molecular Characterization of the Myxoma Virus Genome", *Virology* 170:147–159.

Mykytowycz (1953) "An attentuated strain of the myxomatosis virus recovered from the field", *Nature* 172:448–449.

Stamenkovic et al., (1990) "The B cell antigen CD75 is a cell surface sialyltransferase" *J. Exp. Med.* 172:641–643.

Bast et al., (1992) "The HB–6, Cdw75 and CD76 differentiation antigens are unique cell–surface carbohydrate determinants generated by the β–galactoside α2,6–sialyltransferase" *J. Cell Biol.* 116:423–435.

Bouvier (1954) Quelques remarques sur la myxomatose *Bulletin de L'Office International des Epizooites* 46:76–77.

Jackson, R.J. and Bults, H.G. (1992) "A myxoma virus intergenic transient dominant selection vector" *J. Gen Virol.* 73:3241–3245.

Sticher, U. et al., (1988) "Purification of α2,6–sialyltransferase from rat liver by dye chromatography" *Biochem J.* 253:577–580.

Paulson et al., "Purification of a Sialyltransferase from Bovine Colostrum by Affinity Chromatography on CDP–agarose" *J. Biol. Chem.*, 252(7):2356–2362 (1977).

Niemela et al., "Complementary Acceptor and Site Specificities of Fuc–TIV and Fuc–TVII Allow Effective Biosynthesis of Sialyl–TriLex and Related Polylactosamines Present on Glycoprotein Counterreceptors of Selectins", *J. Biol. Chem.*, 273(7):4021–4026 (1998).

Abbas et al., "Tumor–Associated Oligosaccharides 1: Synthesis of Sialyl–Lewis$^a$ Antigenic Determinant" *Proc. Japanese–German Symp.* Berlin, pp. 22–23 (1988).

Baisch et al., "Enzymatic Fucosylations with Purine–Diphosphate–Fucoses (PDP–Fucosos)" *Bioorganic and Medicinal Chemistry Letters* 6(24):2953–2956 (1996).

(List continued on next page.)

*Primary Examiner*—Ponnathapu Achutamurthy
*Assistant Examiner*—Manjunath N. Rao
*Attorney, Agent, or Firm*—Burns, Doane, Swecker & Mathis, LLP

[57] ABSTRACT

A method of preparation of lysate having α2,3-sialyltransferase activity is disclosed. A cell culture having essentially no endogenous expression of eukaryotic α2,3-sialyltransferase is infected with myxoma virus. The harvested triton lysates include significant quantities of a protein having eukaryotic α2,3-sialyltransferase activity. Compositions having in vitro α2,3-sialyltransferase activity and comprising a protein extract of lysates of the aforementioned lysates are also provided for.

18 Claims, 3 Drawing Sheets

OTHER PUBLICATIONS

Barsoum et al., "Production of Autoantibodies by Immunization with Rabbit Transferrin Modified at its Glycosidic Moiety" *Mol. Immunol.*, 18(5):367–372 (1981).

Baumberger et al., "Synthesis of N–Acetyl–4–deoxyneuraminic Acid" *Helv. Chim. Acta*, 69:1535–1541 (1986).

Beau et al., "Metabolism of 4–O–Methyl–N–acetylneuraminic Acid a Synthetic Sialic Acid" *Eur. J. Biochem.*, 106:531–540 (1980).

Bergh et al., "Aglycon specificity of fetal calf liver and ovine and porcine submaxillary gland α– N–acetylgalactosaminide α2→6 sialyltransferase" *Eur. J. Biochem.*, 136:113–118 (1983).

Beyer et al., "Glycosyltransferases and Their Use in Assessing Oligosaccharide Structure and Structure–Function Relationships" *Adv. Enzymol.*, 52:23–35 (1981).

Brandley et al., "Carbohydrate Ligands of the LEC Cell Adhesion Molecules" *Cell*, 63:861–863 (1990).

Brossmer et al., "Enzymic Synthesis of 5–Acetamido–9–Azido–3, 5, 9–Trideoxy–D–glycero–D–galacto–2–nonulosonic acid, a 9–Azido–9–Deoxy Derivative of N–Acetylneuraminic Acid" *Biochem. Biophys. Res. Comm.*, 96(3):1282–1289 (1980).

Christian et al., "On the Side–Chain Conformation of N–Acetylneuraminic Acid and its Epimers at C–7, C–8, and C–7,8" *Carbohydr. Res.*, 162:1–11 (1987).

Christian et al., "The Side–Chain Conformations of N–Acetyl–7–,8–,9–Deoxy–, and –4,7–Dideoxy––Neuraminic Acid and Their Effect of the Activation of CTP:N–Acylneuraminic Acid Cytidylyl–Transferase" *Carbohydr. Res.*, 194:49–61 (1989).

Conradt et al., "Preparation of 9–fluoro–9–deoxy–N–[2–$^{14}$C]acetylneuraminic acid Activation and transfer onto asialo–$\alpha_1$–acid glycoprotein" *FEBS Lett.*, 170(2):295–300 (1984).

Conradt et al., "Purification to Homogeneity of a Porcine Liver Galβ1–3GalNAc–Rα2–3 Sialyltransferase" *Japanese–German Symp.* pp. 104–105 Berlin (1988).

de Heij, et al., "Biosynthesis of Disialylated β–D–Galactopyranosyl–(1→3)–2–Acetamido–2–Deoxy–β–D–Glucopyranosyl Oligosaccharide Chains. Identification of a β–D–Galactoside α–(2→3) and a 2–Acetamido–2–Deoxy–β–D–Glucoside α–(2→6)–Sialyltransferase in Regenerating Rat Liver and Other Tissues" *Carbohydr. Res.*, 149:85–99 (1986).

Feizi, "Carbohydrate differentiation antigens: probable ligands for cell adhesion molecules" *TIBS*, 16:84–86 (1991).

Fügedi et al.,"Thioglycosides as Glycosylating Agents in Oligosaccharide Synthesis" *Glycoconj. J.*, 4:97–108 (1987).

Fung et al., "Active Specific Immunotherapy of a Murine Mammary Adenocarcinoma Using a Synthetic Tumor–associated Glycoconjugate" *Cancer Res.*, 50:4308–4314 (1990).

Gokhale et al., "Chemical synthesis of GDP–fucose analogs and their utilization by the Lewis α(1→4) fucosyltransferase" *Can J. Chem.* 68(7):1063–1071 (1990).

Gross et al., "N–Acetyl–4–deoxy–D–neuraminic Acid is Activated and Transferred on to Asialoglycoprotein" *Glycoconj. J.*, 4:145–156 (1987).

Gross et al., "Activation and transfer of novel synthetic 9–substituted sialic acids" *Eur. J. Biochem.*, 168:595–602 (1987).

Gross et al., "Interaction of N–Acetyl–4–epi–D–neuraminic Acid with Key Enzymes of Sialic Acid Metabolism" *Biochemistry*, 27:4279–4283 (1988).

Gross et al., "Enzymatic introduction of a fluorescent sialic acid into oligosaccharide chains of glycoproteins" *Eur. J. Biochem.*, 177:583–589 (1988).

Gross et al., "Inhibition of N–acetylneuraminate lyase by N–acetyl–4–oxo–D–neuraminic acid" *FEBS Lett.*, 232(1):145–147 (1988).

Hagedorn et al., XIIIth Carbohydr. Symp., Ithaca (1986) A4.

Hakomori, Sen–itiroh, "Aberrant glycosylation in tumors and tumor–associated carbohydrate antigens" *Adv. Cancer Res.*, 52:257–263 (1989).

Handa et al., "Modification of Sialic Acid Carboxyl Group of Ganglioside" *J. Biochem.*, 95(5):1323–1329 (1984).

Hasegawa et al., "Synthetic Studies on Sialoglycoconjugates 4: Synthesis of 5–Acetamido–3, 5–Dideoxy–D–Galacto–2–Octulosonic Acid Derivatives and Analogs" *J. Carbohydr. Chem.*, 8(1):135–144 (1989).

Hasegawa et al., "Synthetic Studies on Sialoglycoconjugates 7: Synthesis of N–Acetylneuraminic Acid Derivatives and Analogs" *J. Carbohydr. Chem.*, 8(4):579–583, 596 (1989).

Haverkamp et al., "Improved Synthesis of CMP–Sialates Using Enzymes from Frog Liver and Equine Submandibular Gland" *Hoppe–Seyler's Z. Physiol. Chem.*, 360:159–166 (1979).

Henningsson et al., "T cell recognition of a tumor–associated glycoprotein and its synthetic carbohydrate epitopes: stimulation of anticancer T cell immunity in vivo" *Cancer Immunol. Immunother.*, 25:231–241 (1987).

Higa et al., "Sialylation of Glycoprotein Oligosaccharides with N–Acetyl–, N–Glycolyl, and N–O–Diacetylneuraminic Acids" *J. Biol. Chem.*, 260(15):8838–8849 (1985).

Horowitz, The Glycoconjugates, Index to vol. I, New York Academic Press (1977, 1978, 1982, 1983).

Houghton et al., *Symposium on Gangliosides and Cancer*, pp. 233–238, VCH Publishers (1988).

Howard, "Towards Better Carbohydrate Vaccines"; Proceedings of a meeting organized by the World Health Organization, R. Bell, G. Torrigani, Editors, pp. 221–231, Wiley, Chichester (1987).

Irie et al., *Symposium on Gangliosides and Cancer*, pp. 249–257, VCH Publishers (1988).

Joziasse et al., "Purification and Enzymatic Characterization of CMP–sialic Acid: β–Galactosyl1→3–N–Acetylgalactosaminide α2→3–Sialyltransferase from Human Placenta" *J. Biol. Chem.*, 260(8):4941–4951 (1985).

Kameyama et al., "Total Synthesis of sialyl Lewis X" *Carbohydr. Res.*, 209:cl–c4 (1991).

Le et al., "Analysis by capillary electrophoresis–laser–induced fluorescence detection of oligosaccharides produced from enzyme reactions" *J. Chromatography A*. 716:215–220 (1995).

Livingston et al., "Vaccines containing purified GM2 ganglioside elicit GM2 antibodies in melanoma patients" *Proc. Natl. Acad. Sci.* (USA), 84:2911–2915 (1987).

Mack et al., "Synthesis of 6–Thiosialic Acids and 6–Thio–N–Acetyl–D–Neuraminic Acid" *Tetrahedron Lett.*, 28(2):191–194 (1987).

Nakajima et al., "Synthesis of N–Acetyl–3–fluoro–neuraminic Acids" *Agric. Biol. Chem.*, 52(5):1209–1215 (1988).

Nakamura et al., "Biochemical Properties of N–Methylamides of Sialic Acids in Gangliosides" *J. Biochem*, 99(1):219–226 (1986).

Naor et al., "Immune Response to Chemically Modified Antigens" *Prog. Allergy*, 22:108–146 (1977).

Okamoto et al., "Glycosidation of Sialic Acid" *Tetrahedron*, 46(17):5835–5839 (1990).

Ørskov et al., "Form Variation in *Escherichia coli* K1: Determined by O–Acetylation of the Capsular Polysaccharide" *J. Exp. Med.*, 149:669–685 (1979).

Paulsen, "Advances in Selective Chemical Syntheses of Complex Oligosaccharides" *Angewandte Chemie Intl. Ed. Eng.*, 21(3):155–157,170–173 (1982).

Paulsen et al., "Synthese von α–D–glycero–D–galacto–2–Octulonsäure und 5–Acetamido–5–desoxy–β–D–erythro–L–gluco–2–nonul onsäure" *Liebigs Ann. Chem.*, pp. 277–279 (1988).

Paulson et al., "Biosynthesis of a disialylated sequence in N–linked oligosaccharides: identification of an N–acetylglucosaminide (α2→6)–sialyltransferase in Golgi apparatus from rat liver" *Eur. J. Biochem.*, 140:523–530 (1984).

Paulson, "Interactions of Animal Viruses with Cell Surface Receptors" *The Receptors*, vol. II Conn Ed., N.Y. Acad. Press, pp. 131–219 (1985).

Reuter et al., "Suggestions on the Nomenclature of Sialic Acids" *Glycoconjugate J.*, 5:133–135 (1988).

Sadler et al., "Purification to Homogeneity of a β–Galactoside α 2→ 3 Sialyltransferase and Partial Purification of an α–N–Acetylgalactosaminide α2→ 6 Sialyltransferase from Porcine Submaxillary Glands" *J. Biol. Chem.*, 254(11):4434–4442 (1979).

Sadler et al., "Purification to Homogeneity and Enzymatic Characterization of an α–N–Acetylgalactosaminide α 2→ 6 Sialyltransferase from Porcine Submaxillary Glands" *J. Biol. Chem.*, 254(13):5934–5941 (1979).

Salunkhe et al., "A New Useful Approach to the Epimers at C–7 and C–7,8 of N–Acetylneuraminic Acid" *Liebigs Ann. Chem.*, pp. 187–189 (1988).

Schauer, R., "Sialic Acids Chemistry, Metabolism and Function" *Cell Biology Monographs*, vol. 10, Springer–Verlag (1982).

Schengrund et al., "Binding of *Vibrio cholera* Toxin and the Heat–labile Enterotoxin of *Escherichia coli* to $G_{M1}$, Derivatives of $G_{M1}$, and Nonlipid Oligosaccharide Polyvalent Ligands" *J. Biol. Chem.*, 264(22): 13233–13237 (1989).

Schmidt, "New Methods for the Synthesis of Glycosides and Oligosaccharides– Are There Alternatives to the Koenigs–Knorr Method?" *Angew. Chem. Int. Ed. Engl.*, 25:212–215, 232–235 (1986).

Sharma et al., "General Methods for Modification of Sialic Acid at C–9. Synthesis of N–Acetyl–9–Deoxy–9–Fluoroneuraminic Acid" *Carbohydr. Res.*, 175:25–34 (1988).

Srivastava et al., "Enzymatic Transfer of a Preassembled Trisaccharide Antigen to Cell Surfaces Using a Fucosyltransferase" *J. Biol. Chem.* 267(31):22356–22361 (1992).

Stangier et al., "Fucosyltransferase–catalyzed formation of L–galactosylated Lewis structures" *Carbohydrate Res.* 305:511–515 (1998).

Toone et al., "Enzyme–Catalyzed Synthesis of Carbohydrates" *Tetrahedron*, 45(17):5365–5369 (1989).

Zbiral et al., "Strukturelle Abwandlungen an N–Acetylneuraminsäure, $3^1$ Synthese von 7–epi–, 8–epi– und 7,8–Bis–epi–N–Acetylneuraminsäure—ihr Verhalten gegenüer Cytidin–Monophosphat–Sialinsäuresynthetase" *Monatsh. Chem.*, 116:87–91 (1985).

Zbiral et al., "Strukturelle Abwandlungen an N–Acetylneuraminsäuren, 8[1] Synthase von 7–, 8–, 9–Desoxy– und 4,7–Didesoxyneuraminsäure" *Monatsh. Chem.*, 119:127–131 (1988).

Zbiral et al., "Synthesis of the 4–acetamido–4–deoxy analogue of N–acetylneuraminic acid and its behaviour towards CMP–sialate synthase" *Carbohydr. Res.*, 194:c15–c18 (1989).

Kajihara et al., "A novel α–2,6–sialyltransferase: Transfer of Sialic Acid to Fucosyl and Sialyl Trisaccharides" *J. Org. Chem.* 61:8632–8635 (1996).

Goebel et al., (1990) Appendix to "The Complete DNA Sequence of Vaccinia Virus" *Virology* 179:517–563.

GenBank M35027 (Aug. 3, 1993), pp 1–90.

SEQUENCE LISTING

```
<160> NUMBER OF SEQ ID NOS: 13

<210> SEQ ID NO 1
<211> LENGTH: 24
<212> TYPE: DNA
<213> ORGANISM: Myxoma virus

<400> SEQUENCE: 1

gggatccath tcyagrcaya arcg                                             24


<210> SEQ ID NO 2
<211> LENGTH: 24
<212> TYPE: DNA
<213> ORGANISM: Myxoma virus
<220> FEATURE:
<221> NAME/KEY: misc_feature
<222> LOCATION: (16)..(24)
<223> OTHER INFORMATION: Nucleotide at position 16 is n wherein
      n = a, t, c or g.

<400> SEQUENCE: 2

gggatccgcr cayaanccda tcat                                             24


<210> SEQ ID NO 3
<211> LENGTH: 4713
<212> TYPE: DNA
<213> ORGANISM: Myxoma virus
<220> FEATURE:
<221> NAME/KEY: CDS
<222> LOCATION: (1)..(549)
<220> FEATURE:
<221> NAME/KEY: CDS
<222> LOCATION: (1515)..(2081)
<220> FEATURE:
<221> NAME/KEY: CDS
<222> LOCATION: (2084)..(3745)
<220> FEATURE:
<221> NAME/KEY: CDS
<222> LOCATION: (3778)..(4434)
<220> FEATURE:
<221> NAME/KEY: CDS
<222> LOCATION: (4440)..(4712)

<400> SEQUENCE: 3

gga tcc aac gtc gtc gta tct gtg gcg ttg ttc gaa gaa gcg gag ggg       48
Gly Ser Asn Val Val Val Ser Val Ala Leu Phe Glu Glu Ala Glu Gly
  1               5                  10                  15

cct cgg gtt ccg tta ctc aga acg att cac aac gga ggc gtt att atc       96
Pro Arg Val Pro Leu Leu Arg Thr Ile His Asn Gly Gly Val Ile Ile
             20                  25                  30
```

-continued

```
tcc aga cat aaa cgg ttg cat aag gaa ctc ccc agt caa gat tgg ttt      144
Ser Arg His Lys Arg Leu His Lys Glu Leu Pro Ser Gln Asp Trp Phe
         35                  40                  45

tct ttt tac gtg gaa gta ttc cac tgc tac act tcc gtg ata tac gcg      192
Ser Phe Tyr Val Glu Val Phe His Cys Tyr Thr Ser Val Ile Tyr Ala
     50                  55                  60

gta gtt gac gga gcc gtt cta tac gca aac gcc gat tac aaa aca cat      240
Val Val Asp Gly Ala Val Leu Tyr Ala Asn Ala Asp Tyr Lys Thr His
 65                  70                  75                  80

tgt acg ata agc gat ggc cga cga cat agg gaa gac gtt acg gac gat      288
Cys Thr Ile Ser Asp Gly Arg Arg His Arg Glu Asp Val Thr Asp Asp
                 85                  90                  95

tgt ctg tgt tgt cac gta tct cct caa att cgt acg ttc ggt aca cag      336
Cys Leu Cys Cys His Val Ser Pro Gln Ile Arg Thr Phe Gly Thr Gln
            100                 105                 110

gta atg gag aac gta gag tgt cgg gtg gta cgg gat ggt tta tgt atc      384
Val Met Glu Asn Val Glu Cys Arg Val Val Arg Asp Gly Leu Cys Ile
        115                 120                 125

gaa ata aaa cac gtg gga aaa ttc gga gca tcg tgc gta ggt gcg tat      432
Glu Ile Lys His Val Gly Lys Phe Gly Ala Ser Cys Val Gly Ala Tyr
    130                 135                 140

aat acg cgg tat ata aaa ata gcg ata ggg tcg gtg tac gat atc att      480
Asn Thr Arg Tyr Ile Lys Ile Ala Ile Gly Ser Val Tyr Asp Ile Ile
145                 150                 155                 160

cta aaa cag gac ggg atg tcc gga aag aag cga cat agt tgc tac gtg      528
Leu Lys Gln Asp Gly Met Ser Gly Lys Lys Arg His Ser Cys Tyr Val
                165                 170                 175

tac gga atc acc cga cgg tag gcttgcgaaa tagtgtattg tttttatca          579
Tyr Gly Ile Thr Arg Arg
            180

gagttagcgt atacaaagga tcgtcttatt ttggatcata cgttcgatga tcgttttctc    639

cgcgtttacg tcgtgaatgg agttttgcat ggcacgcata gtatagccgt tgtaataatg    699

gataaattgg ttaggccccc cattggggta cccgaatccc gtaatcgtta cgccctggca    759

cacgtgtaac gcggtcacga gcgcgaccat tcccatcgta ggaacgtgca acgttccgga    819

cgttgtctgt atacgcaacg ccgcatcgta cgtatatttc ggatgtagga ttcgtacgaa    879

cgccggacgc gcgcgccacg tgcgaggcgg tttcttccaa aatctagaca ggtcgacgcg    939

tgcgttgttc gtaagcatgt tatatagcca gtataagtcg gcggacttga acggaaccat    999

tacaaacagc gtcgtattat cgttttcttt cacggaatcc gattgggcgg attccgggta   1059

gaacatacgt atcgtcgttt ttgtcccaac gtctcgttcg aaggcacgaa cgggagcgtc   1119

gtttaaccga aacaccacgt tgtacgagtc gatgattcgt cctaaagatc tattgtgtaa   1179

gttataacta tttcctacga cgatacattg tttgccgtat aagaggaaat taggaagatg   1239

tccaggaatc ttttctaaca gacgacgtat ctgcgcttcc tctcctttta gcccgtacgg   1299

taaacgtctt tcgaacgtat tattgtgggt tacaaatacg tttgtgacgg atacgttgtt   1359

cgttccgtgg tttaccacgg acattttcaa cgacattacg aacaacgcaa ctgcggtaca   1419

tgcgtacacc atcgtgcatc gtttaaagaa atacatatcg cagaagcaag atttttttg    1479

tgttttagtc tacccaacgt acgcgataga acact atg agc aac tac gta aag      1532
                                       Met Ser Asn Tyr Val Lys
                                           185

ttc gac gta tcg atc gaa gat gac tgt atc aat ata acg gtc agt aac     1580
Phe Asp Val Ser Ile Glu Asp Asp Cys Ile Asn Ile Thr Val Ser Asn
190                 195                 200                 205
```

-continued

```
act agt tta ccc atc cac gta aag acc gtc ccc aaa cgc aca cat cgg     1628
Thr Ser Leu Pro Ile His Val Lys Thr Val Pro Lys Arg Thr His Arg
                210                 215                 220

gac aat tac gtg ttt aaa aac act ata gac gcc tcg gac gat atc gtc     1676
Asp Asn Tyr Val Phe Lys Asn Thr Ile Asp Ala Ser Asp Asp Ile Val
            225                 230                 235

tct atc cta cac aac tat ata tgg tac aga gga ttt ata ggt ctg ccg     1724
Ser Ile Leu His Asn Tyr Ile Trp Tyr Arg Gly Phe Ile Gly Leu Pro
        240                 245                 250

aac aaa tac ggt agg gtg ttc aaa gaa cta aag ctc ttc gac atc gac     1772
Asn Lys Tyr Gly Arg Val Phe Lys Glu Leu Lys Leu Phe Asp Ile Asp
    255                 260                 265

gca aag acc aaa tac gga gat ata aat act tta ttt ttc atg tta aat     1820
Ala Lys Thr Lys Tyr Gly Asp Ile Asn Thr Leu Phe Phe Met Leu Asn
270                 275                 280                 285

tta aac tcg gat cgt tgc tgc agg aat ttt ttc aat ttc gta aca cta     1868
Leu Asn Ser Asp Arg Cys Cys Arg Asn Phe Phe Asn Phe Val Thr Leu
                290                 295                 300

caa aaa act ata ttc aaa cac acg gtt acc gta tac aac tgc atc gaa     1916
Gln Lys Thr Ile Phe Lys His Thr Val Thr Val Tyr Asn Cys Ile Glu
            305                 310                 315

atg ata gga tta tgt gcc ctg gtg gcg gaa caa tgg aaa aat aat aac     1964
Met Ile Gly Leu Cys Ala Leu Val Ala Glu Gln Trp Lys Asn Asn Asn
        320                 325                 330

aaa tgt tta aat tgg cgt atc gta gta gat gaa atg ttt agg ttc atc     2012
Lys Cys Leu Asn Trp Arg Ile Val Val Asp Glu Met Phe Arg Phe Ile
    335                 340                 345

gac cct gac atg tta gaa aag atc aga acg gta ctc caa gaa cga ttg     2060
Asp Pro Asp Met Leu Glu Lys Ile Arg Thr Val Leu Gln Glu Arg Leu
350                 355                 360                 365

gcg tac gag gac ctg tcg taa ca atg acg ggt cgt tac gcc atc cgg      2107
Ala Tyr Glu Asp Leu Ser        Met Thr Gly Arg Tyr Ala Ile Arg
                370                    375                 380

ttg tta gaa tcc att aga aat tta cag gat aag acc acc tta tgc gac     2155
Leu Leu Glu Ser Ile Arg Asn Leu Gln Asp Lys Thr Thr Leu Cys Asp
                385                 390                 395

gtt acg tta gtt acg gac gat gat gtg tct ata cat gcg cat aaa ctt     2203
Val Thr Leu Val Thr Asp Asp Asp Val Ser Ile His Ala His Lys Leu
            400                 405                 410

atc ttg tcc gcg tct tct acg tat ttc gaa tat atg ttt tcg cac gac     2251
Ile Leu Ser Ala Ser Ser Thr Tyr Phe Glu Tyr Met Phe Ser His Asp
        415                 420                 425

ttt ata gaa aaa gac aga aac gta ata aac gtg tgt gtc gaa tat cgt     2299
Phe Ile Glu Lys Asp Arg Asn Val Ile Asn Val Cys Val Glu Tyr Arg
    430                 435                 440

gcc ttg ttg cac cta atc aat ttt ata tac tca gga acc tta cgt ttg     2347
Ala Leu Leu His Leu Ile Asn Phe Ile Tyr Ser Gly Thr Leu Arg Leu
445                 450                 455                 460

acg gat gat acg gtg gac tgt att cta gta gcc gcc gat tac cta cag     2395
Thr Asp Asp Thr Val Asp Cys Ile Leu Val Ala Ala Asp Tyr Leu Gln
                465                 470                 475

ata cta gag gcg agt gaa ttg gcg gaa aac ttt ata ctc gcc cgt cta     2443
Ile Leu Glu Ala Ser Glu Leu Ala Glu Asn Phe Ile Leu Ala Arg Leu
            480                 485                 490

aga gcg gag aat tgc ctc cat tac tac gaa ttt tcc aaa cgt tac aac     2491
Arg Ala Glu Asn Cys Leu His Tyr Tyr Glu Phe Ser Lys Arg Tyr Asn
        495                 500                 505

aga cga cat ata ttc aac gtg gta atc acg acg att ata cac aac atc     2539
Arg Arg His Ile Phe Asn Val Val Ile Thr Thr Ile Ile His Asn Ile
    510                 515                 520
```

-continued

```
gtc agt gtg tta aga caa ccc aat ttt aag acc atc gag tta tgc gat     2587
Val Ser Val Leu Arg Gln Pro Asn Phe Lys Thr Ile Glu Leu Cys Asp
525                 530                 535                 540

ctg cag aat ata tta tcc agc gac gat tta aac gtg ata gac gag gat     2635
Leu Gln Asn Ile Leu Ser Ser Asp Asp Leu Asn Val Ile Asp Glu Asp
                545                 550                 555

gta tgc gcc gtc gtc tta gtc acc tgg ttg aag caa aac aac atg gaa     2683
Val Cys Ala Val Val Leu Val Thr Trp Leu Lys Gln Asn Asn Met Glu
            560                 565                 570

gat tgc cca tcc gtt tta ctg gaa caa gta cgg atg tcg tta ctc tca     2731
Asp Cys Pro Ser Val Leu Leu Glu Gln Val Arg Met Ser Leu Leu Ser
        575                 580                 585

atg tct gtg aaa aac ctt cta cta aaa acc cct tgc ata cgt aat aaa     2779
Met Ser Val Lys Asn Leu Leu Leu Lys Thr Pro Cys Ile Arg Asn Lys
    590                 595                 600

cga tac gta cag tct ctc gcc aaa tta gac cat tcc cct aga cct ccc     2827
Arg Tyr Val Gln Ser Leu Ala Lys Leu Asp His Ser Pro Arg Pro Pro
605                 610                 615                 620

act cag ggg tgt atc ctg tcg ata ggg ggt cgt aaa tac tac gac gat     2875
Thr Gln Gly Cys Ile Leu Ser Ile Gly Gly Arg Lys Tyr Tyr Asp Asp
                625                 630                 635

atc acg tcc agt ccc gta gaa ttg tat tct ccc gtg gac gac gta tgg     2923
Ile Thr Ser Ser Pro Val Glu Leu Tyr Ser Pro Val Asp Asp Val Trp
            640                 645                 650

acg acc gtg tcc tac tta cca acg cac cga cag ttc ttt agc gtc gcc     2971
Thr Thr Val Ser Tyr Leu Pro Thr His Arg Gln Phe Phe Ser Val Ala
        655                 660                 665

gta ttg gat ttt gtc gta tac gtc gtg ggt ggg tta cag gac agt gta     3019
Val Leu Asp Phe Val Val Tyr Val Val Gly Gly Leu Gln Asp Ser Val
    670                 675                 680

tcc gtc gcg tcc gtg tcc agt tac gac gta aag acg aac gaa tgg aaa     3067
Ser Val Ala Ser Val Ser Ser Tyr Asp Val Lys Thr Asn Glu Trp Lys
685                 690                 695                 700

gag tgt cct cct ctt aaa agt ccc cga cac ggg tgc gga tta gtg gtc     3115
Glu Cys Pro Pro Leu Lys Ser Pro Arg His Gly Cys Gly Leu Val Val
                705                 710                 715

ttg cga gac aaa ctg ata gtg ata gga gga aaa gga aga aac tcc tat     3163
Leu Arg Asp Lys Leu Ile Val Ile Gly Gly Lys Gly Arg Asn Ser Tyr
            720                 725                 730

ctg aaa gac gtc gac tac tgg aga ccg acg tac gcc acg tgg aga aaa     3211
Leu Lys Asp Val Asp Tyr Trp Arg Pro Thr Tyr Ala Thr Trp Arg Lys
        735                 740                 745

ctg tgc tct ctc cgc gag gcg agg acg aac gtg gga gcc gcc gtc gta     3259
Leu Cys Ser Leu Arg Glu Ala Arg Thr Asn Val Gly Ala Ala Val Val
    750                 755                 760

cgc aac aaa gtc tat aca ata ggc ggg ata cgt agc gtc gag gaa ccg     3307
Arg Asn Lys Val Tyr Thr Ile Gly Gly Ile Arg Ser Val Glu Glu Pro
765                 770                 775                 780

agt cga ttg gaa tgc atc gat acc gta gag tgt tta cag aac aac aaa     3355
Ser Arg Leu Glu Cys Ile Asp Thr Val Glu Cys Leu Gln Asn Asn Lys
                785                 790                 795

tgg gtc gcg aag aag tcg tta ccc gaa cca aag gcc tgt ttg gcc gtg     3403
Trp Val Ala Lys Lys Ser Leu Pro Glu Pro Lys Ala Cys Leu Ala Val
            800                 805                 810

gcg cct tac aaa cat ttc att tac gcg gcg ggt gga tac gcc atc aac     3451
Ala Pro Tyr Lys His Phe Ile Tyr Ala Ala Gly Gly Tyr Ala Ile Asn
        815                 820                 825

ggc agg ggc acc gtc gtt act aaa acg aac acg ttg tac atg tat aac     3499
Gly Arg Gly Thr Val Val Thr Lys Thr Asn Thr Leu Tyr Met Tyr Asn
```

-continued

```
    830                 835                 840

gtg gaa ttg gac gac tgg ttt tac cta cct atg atg gag ctg tct aga      3547
Val Glu Leu Asp Asp Trp Phe Tyr Leu Pro Met Met Glu Leu Ser Arg
845                 850                 855                 860

aac gac gcg tct ctc tgt gtg tta ggt aaa gac ctc tac gtt gta ggg      3595
Asn Asp Ala Ser Leu Cys Val Leu Gly Lys Asp Leu Tyr Val Val Gly
                865                 870                 875

ggt ttt gta gga tcg gga tac aca aat tcc gtg gaa aaa tac aac cac      3643
Gly Phe Val Gly Ser Gly Tyr Thr Asn Ser Val Glu Lys Tyr Asn His
            880                 885                 890

aag acc aat aat tgg gaa cga att ata cca tgt aaa tcg ccc aag tac      3691
Lys Thr Asn Asn Trp Glu Arg Ile Ile Pro Cys Lys Ser Pro Lys Tyr
        895                 900                 905

gga cac tgt tcc gtc gtg tta aac cac gag tgc cct tgg aaa cat ctg      3739
Gly His Cys Ser Val Val Leu Asn His Glu Cys Pro Trp Lys His Leu
    910                 915                 920

cgc taa aaactaaaat ataacgcgga agaagagaga cg atg cgt gtg tta agt      3792
Arg                                         Met Arg Val Leu Ser
925                                                     930

att tta gcg tta tta tct aca gta gcc tac gct tac tcc gtt cgc tgt      3840
Ile Leu Ala Leu Leu Ser Thr Val Ala Tyr Ala Tyr Ser Val Arg Cys
            935                 940                 945

aca aat aca acg acg gta gcc gaa cat gta aac gtt act att agt tgc      3888
Thr Asn Thr Thr Thr Val Ala Glu His Val Asn Val Thr Ile Ser Cys
        950                 955                 960

aat aaa act agc agt agt agt agt ttg ttc cat ctt ata acg tgg aaa      3936
Asn Lys Thr Ser Ser Ser Ser Ser Leu Phe His Leu Ile Thr Trp Lys
    965                 970                 975

aaa aat aat gaa acg act ata gcg ggg tac gga cca agt ggc gca acc      3984
Lys Asn Asn Glu Thr Thr Ile Ala Gly Tyr Gly Pro Ser Gly Ala Thr
980                 985                 990                 995

att aaa gat gcg agc aaa ata gag tat tta tcc act gga tac aac acg      4032
Ile Lys Asp Ala Ser Lys Ile Glu Tyr Leu Ser Thr Gly Tyr Asn Thr
               1000                1005                1010

tcc act atc ttg ata aaa aat gta agc gcg gaa gat agc gga ctt tac      4080
Ser Thr Ile Leu Ile Lys Asn Val Ser Ala Glu Asp Ser Gly Leu Tyr
           1015                1020                1025

tac tgt ata ttc aac tcg ttc tct acc gaa cct agc gaa gaa gga acg      4128
Tyr Cys Ile Phe Asn Ser Phe Ser Thr Glu Pro Ser Glu Glu Gly Thr
       1030                1035                1040

gta cgg gta aac gta acg aca tct agt gca acg act act tta caa caa      4176
Val Arg Val Asn Val Thr Thr Ser Ser Ala Thr Thr Thr Leu Gln Gln
   1045                1050                1055

cct caa cct cag gct tta cga acg acc cgt ggt cga tcg act aat cga      4224
Pro Gln Pro Gln Ala Leu Arg Thr Thr Arg Gly Arg Ser Thr Asn Arg
1060                1065                1070                1075

tcg acg tcg cgt cac gta tcg cgt acc tcg acg cat cac gta ggt gac      4272
Ser Thr Ser Arg His Val Ser Arg Thr Ser Thr His His Val Gly Asp
               1080                1085                1090

gga tcc tta acg gtg gaa acg aga cag tat aaa tac tca tct tcg tcc      4320
Gly Ser Leu Thr Val Glu Thr Arg Gln Tyr Lys Tyr Ser Ser Ser Ser
           1095                1100                1105

tct tcc tca tcc tcc agc tgg acg agt agc gca gga tct cgt aac gta      4368
Ser Ser Ser Ser Ser Ser Trp Thr Ser Ser Ala Gly Ser Arg Asn Val
       1110                1115                1120

ccg agc tta ttt aaa ctc att ttc gta ata aaa atg att ttt tat atc      4416
Pro Ser Leu Phe Lys Leu Ile Phe Val Ile Lys Met Ile Phe Tyr Ile
   1125                1130                1135

cca aat tta atc gga taa atact atg tca aaa cga aac gaa ata gaa cca    4466
```

-continued

```
Pro Asn Leu Ile Gly          Met Ser Lys Arg Asn Glu Ile Glu Pro
1140               1145                1150

ggg gac gtg tta atc gat gca tcg aaa cgg gaa tgg gta ctc ggg gac     4514
Gly Asp Val Leu Ile Asp Ala Ser Lys Arg Glu Trp Val Leu Gly Asp
1155               1160                1165                1170

att ttg gga aag ggt ggg ttt gga tac att tac acg gcc cgt ttg tgt     4562
Ile Leu Gly Lys Gly Gly Phe Gly Tyr Ile Tyr Thr Ala Arg Leu Cys
               1175                1180                1185

tcg gaa gag gaa ttt gac aaa tac gtt ata aaa ata gaa ccg aaa agt     4610
Ser Glu Glu Glu Phe Asp Lys Tyr Val Ile Lys Ile Glu Pro Lys Ser
           1190                1195                1200

aac ggt ccc ttg ttc gta gaa cag gtg ttt tat caa cgg gtg ggt aaa     4658
Asn Gly Pro Leu Phe Val Glu Gln Val Phe Tyr Gln Arg Val Gly Lys
       1205                1210                1215

acc gac atg gtc acg gac tgg tgt aag aaa aat aac tta ccg tat ttg     4706
Thr Asp Met Val Thr Asp Trp Cys Lys Lys Asn Asn Leu Pro Tyr Leu
   1220                1225                1230

gga att c                                                           4713
Gly Ile
1235


<210> SEQ ID NO 4
<211> LENGTH: 182
<212> TYPE: PRT
<213> ORGANISM: Myxoma virus

<400> SEQUENCE: 4

Gly Ser Asn Val Val Val Ser Val Ala Leu Phe Glu Glu Ala Glu Gly
  1               5                  10                  15

Pro Arg Val Pro Leu Leu Arg Thr Ile His Asn Gly Gly Val Ile Ile
            20                  25                  30

Ser Arg His Lys Arg Leu His Lys Glu Leu Pro Ser Gln Asp Trp Phe
        35                  40                  45

Ser Phe Tyr Val Glu Val Phe His Cys Tyr Thr Ser Val Ile Tyr Ala
     50                  55                  60

Val Val Asp Gly Ala Val Leu Tyr Ala Asn Ala Asp Tyr Lys Thr His
 65                  70                  75                  80

Cys Thr Ile Ser Asp Gly Arg Arg His Arg Glu Asp Val Thr Asp Asp
                 85                  90                  95

Cys Leu Cys Cys His Val Ser Pro Gln Ile Arg Thr Phe Gly Thr Gln
            100                 105                 110

Val Met Glu Asn Val Glu Cys Arg Val Val Arg Asp Gly Leu Cys Ile
        115                 120                 125

Glu Ile Lys His Val Gly Lys Phe Gly Ala Ser Cys Val Gly Ala Tyr
    130                 135                 140

Asn Thr Arg Tyr Ile Lys Ile Ala Ile Gly Ser Val Tyr Asp Ile Ile
145                 150                 155                 160

Leu Lys Gln Asp Gly Met Ser Gly Lys Lys Arg His Ser Cys Tyr Val
                165                 170                 175

Tyr Gly Ile Thr Arg Arg
            180


<210> SEQ ID NO 5
<211> LENGTH: 188
<212> TYPE: PRT
<213> ORGANISM: Myxoma virus

<400> SEQUENCE: 5
```

-continued

```
Met Ser Asn Tyr Val Lys Phe Asp Val Ser Ile Glu Asp Asp Cys Ile
  1               5                  10                  15

Asn Ile Thr Val Ser Asn Thr Ser Leu Pro Ile His Val Lys Thr Val
             20                  25                  30

Pro Lys Arg Thr His Arg Asp Asn Tyr Val Phe Lys Asn Thr Ile Asp
         35                  40                  45

Ala Ser Asp Asp Ile Val Ser Ile Leu His Asn Tyr Ile Trp Tyr Arg
     50                  55                  60

Gly Phe Ile Gly Leu Pro Asn Lys Tyr Gly Arg Val Phe Lys Glu Leu
 65                  70                  75                  80

Lys Leu Phe Asp Ile Asp Ala Lys Thr Lys Tyr Gly Asp Ile Asn Thr
                 85                  90                  95

Leu Phe Phe Met Leu Asn Leu Asn Ser Asp Arg Cys Cys Arg Asn Phe
            100                 105                 110

Phe Asn Phe Val Thr Leu Gln Lys Thr Ile Phe Lys His Thr Val Thr
        115                 120                 125

Val Tyr Asn Cys Ile Glu Met Ile Gly Leu Cys Ala Leu Val Ala Glu
    130                 135                 140

Gln Trp Lys Asn Asn Asn Lys Cys Leu Asn Trp Arg Ile Val Val Asp
145                 150                 155                 160

Glu Met Phe Arg Phe Ile Asp Pro Asp Met Leu Glu Lys Ile Arg Thr
                165                 170                 175

Val Leu Gln Glu Arg Leu Ala Tyr Glu Asp Leu Ser
            180                 185


<210> SEQ ID NO 6
<211> LENGTH: 553
<212> TYPE: PRT
<213> ORGANISM: Myxoma virus

<400> SEQUENCE: 6

Met Thr Gly Arg Tyr Ala Ile Arg Leu Leu Glu Ser Ile Arg Asn Leu
  1               5                  10                  15

Gln Asp Lys Thr Thr Leu Cys Asp Val Thr Leu Val Thr Asp Asp Asp
             20                  25                  30

Val Ser Ile His Ala His Lys Leu Ile Leu Ser Ala Ser Ser Thr Tyr
         35                  40                  45

Phe Glu Tyr Met Phe Ser His Asp Phe Ile Glu Lys Asp Arg Asn Val
     50                  55                  60

Ile Asn Val Cys Val Glu Tyr Arg Ala Leu Leu His Leu Ile Asn Phe
 65                  70                  75                  80

Ile Tyr Ser Gly Thr Leu Arg Leu Thr Asp Asp Thr Val Asp Cys Ile
                 85                  90                  95

Leu Val Ala Ala Asp Tyr Leu Gln Ile Leu Glu Ala Ser Glu Leu Ala
            100                 105                 110

Glu Asn Phe Ile Leu Ala Arg Leu Arg Ala Glu Asn Cys Leu His Tyr
        115                 120                 125

Tyr Glu Phe Ser Lys Arg Tyr Asn Arg Arg His Ile Phe Asn Val Val
    130                 135                 140

Ile Thr Thr Ile Ile His Asn Ile Val Ser Val Leu Arg Gln Pro Asn
145                 150                 155                 160

Phe Lys Thr Ile Glu Leu Cys Asp Leu Gln Asn Ile Leu Ser Ser Asp
                165                 170                 175

Asp Leu Asn Val Ile Asp Glu Asp Val Cys Ala Val Val Leu Val Thr
            180                 185                 190
```

-continued

```
Trp Leu Lys Gln Asn Asn Met Glu Asp Cys Pro Ser Val Leu Leu Glu
        195                 200                 205

Gln Val Arg Met Ser Leu Leu Ser Met Ser Val Lys Asn Leu Leu Leu
    210                 215                 220

Lys Thr Pro Cys Ile Arg Asn Lys Arg Tyr Val Gln Ser Leu Ala Lys
225                 230                 235                 240

Leu Asp His Ser Pro Arg Pro Pro Thr Gln Gly Cys Ile Leu Ser Ile
                245                 250                 255

Gly Gly Arg Lys Tyr Tyr Asp Asp Ile Thr Ser Ser Pro Val Glu Leu
            260                 265                 270

Tyr Ser Pro Val Asp Asp Val Trp Thr Thr Val Ser Tyr Leu Pro Thr
        275                 280                 285

His Arg Gln Phe Phe Ser Val Ala Val Leu Asp Phe Val Val Tyr Val
    290                 295                 300

Val Gly Gly Leu Gln Asp Ser Val Ser Val Ala Ser Val Ser Ser Tyr
305                 310                 315                 320

Asp Val Lys Thr Asn Glu Trp Lys Glu Cys Pro Pro Leu Lys Ser Pro
                325                 330                 335

Arg His Gly Cys Gly Leu Val Val Leu Arg Asp Lys Leu Ile Val Ile
            340                 345                 350

Gly Gly Lys Gly Arg Asn Ser Tyr Leu Lys Asp Val Asp Tyr Trp Arg
        355                 360                 365

Pro Thr Tyr Ala Thr Trp Arg Lys Leu Cys Ser Leu Arg Glu Ala Arg
    370                 375                 380

Thr Asn Val Gly Ala Ala Val Val Arg Asn Lys Val Tyr Thr Ile Gly
385                 390                 395                 400

Gly Ile Arg Ser Val Glu Glu Pro Ser Arg Leu Glu Cys Ile Asp Thr
                405                 410                 415

Val Glu Cys Leu Gln Asn Asn Lys Trp Val Ala Lys Lys Ser Leu Pro
            420                 425                 430

Glu Pro Lys Ala Cys Leu Ala Val Ala Pro Tyr Lys His Phe Ile Tyr
        435                 440                 445

Ala Ala Gly Gly Tyr Ala Ile Asn Gly Arg Gly Thr Val Val Thr Lys
    450                 455                 460

Thr Asn Thr Leu Tyr Met Tyr Asn Val Glu Leu Asp Asp Trp Phe Tyr
465                 470                 475                 480

Leu Pro Met Met Glu Leu Ser Arg Asn Asp Ala Ser Leu Cys Val Leu
                485                 490                 495

Gly Lys Asp Leu Tyr Val Val Gly Gly Phe Val Gly Ser Gly Tyr Thr
            500                 505                 510

Asn Ser Val Glu Lys Tyr Asn His Lys Thr Asn Asn Trp Glu Arg Ile
        515                 520                 525

Ile Pro Cys Lys Ser Pro Lys Tyr Gly His Cys Ser Val Val Leu Asn
    530                 535                 540

His Glu Cys Pro Trp Lys His Leu Arg
545                 550
```

<210> SEQ ID NO 7
<211> LENGTH: 218
<212> TYPE: PRT
<213> ORGANISM: Myxoma virus

<400> SEQUENCE: 7

```
            Met Arg Val Leu Ser Ile Leu Ala Leu Leu Ser Thr Val
```

-continued

```
        1               5                   10

Ala Tyr Ala Tyr Ser Val Arg Cys Thr Asn Thr Thr Thr Val Ala Glu
     15                  20                  25

His Val Asn Val Thr Ile Ser Cys Asn Lys Thr Ser Ser Ser Ser Ser
 30                  35                  40                  45

Leu Phe His Leu Ile Thr Trp Lys Lys Asn Asn Glu Thr Thr Ile Ala
                 50                  55                  60

Gly Tyr Gly Pro Ser Gly Ala Thr Ile Lys Asp Ala Ser Lys Ile Glu
             65                  70                  75

Tyr Leu Ser Thr Gly Tyr Asn Thr Ser Thr Ile Leu Ile Lys Asn Val
         80                  85                  90

Ser Ala Glu Asp Ser Gly Leu Tyr Tyr Cys Ile Phe Asn Ser Phe Ser
     95                 100                 105

Thr Glu Pro Ser Glu Glu Gly Thr Val Arg Val Asn Val Thr Thr Ser
110                 115                 120                 125

Ser Ala Thr Thr Thr Leu Gln Gln Pro Gln Pro Gln Ala Leu Arg Thr
                130                 135                 140

Thr Arg Gly Arg Ser Thr Asn Arg Ser Thr Ser Arg His Val Ser Arg
            145                 150                 155

Thr Ser Thr His His Val Gly Asp Gly Ser Leu Thr Val Glu Thr Arg
        160                 165                 170

Gln Tyr Lys Tyr Ser Ser Ser Ser Ser Ser Ser Ser Ser Ser Trp Thr
    175                 180                 185

Ser Ser Ala Gly Ser Arg Asn Val Pro Ser Leu Phe Lys Leu Ile Phe
190                 195                 200                 205

Val Ile Lys Met Ile Phe Tyr Ile Pro Asn Leu Ile Gly
                210                 215


<210> SEQ ID NO 8
<211> LENGTH: 91
<212> TYPE: PRT
<213> ORGANISM: Myxoma virus

<400> SEQUENCE: 8

    Met Ser Lys Arg Asn Glu Ile Glu Pro Gly Asp Val Leu Ile Asp
    1               5                   10                  15

Ala Ser Lys Arg Glu Trp Val Leu Gly Asp Ile Leu Gly Lys Gly Gly
                20                  25                  30

Phe Gly Tyr Ile Tyr Thr Ala Arg Leu Cys Ser Glu Glu Glu Phe Asp
            35                  40                  45

Lys Tyr Val Ile Lys Ile Glu Pro Lys Ser Asn Gly Pro Leu Phe Val
        50                  55                  60

Glu Gln Val Phe Tyr Gln Arg Val Gly Lys Thr Asp Met Val Thr Asp
    65                  70                  75

Trp Cys Lys Lys Asn Asn Leu Pro Tyr Leu Gly Ile
80                  85                  90


<210> SEQ ID NO 9
<211> LENGTH: 290
<212> TYPE: PRT
<213> ORGANISM: Myxoma virus

<400> SEQUENCE: 9

Met Tyr Phe Phe Lys Arg Cys Thr Met Val Tyr Ala Cys Thr Ala Val
  1               5                  10                  15

Ala Leu Phe Val Met Ser Leu Lys Met Ser Val Val Asn His Gly Thr
```

-continued

```
            20                  25                  30

Asn Asn Val Ser Val Thr Asn Val Phe Val Thr His Asn Asn Thr Phe
        35                  40                  45

Glu Arg Arg Leu Pro Tyr Gly Leu Lys Gly Glu Glu Ala Gln Ile Arg
    50                  55                  60

Arg Leu Leu Glu Lys Ile Pro Gly His Leu Pro Asn Phe Leu Leu Tyr
65                  70                  75                  80

Gly Lys Gln Cys Ile Val Val Gly Asn Ser Tyr Asn Leu His Asn Arg
                85                  90                  95

Ser Leu Gly Arg Ile Ile Asp Ser Tyr Asn Val Val Phe Arg Leu Asn
            100                 105                 110

Asp Ala Pro Val Arg Ala Phe Glu Arg Asp Val Gly Thr Lys Thr Thr
        115                 120                 125

Ile Arg Met Phe Tyr Pro Glu Ser Ala Gln Ser Asp Ser Val Lys Glu
    130                 135                 140

Asn Asp Asn Thr Thr Leu Phe Val Met Val Pro Phe Lys Ser Ala Asp
145                 150                 155                 160

Leu Tyr Trp Leu Tyr Asn Met Leu Thr Asn Asn Ala Arg Val Asp Leu
                165                 170                 175

Ser Arg Phe Trp Lys Lys Pro Pro Arg Thr Trp Arg Ala Arg Pro Ala
            180                 185                 190

Phe Val Arg Ile Leu His Pro Lys Tyr Thr Tyr Asp Ala Ala Leu Arg
        195                 200                 205

Ile Gln Thr Thr Ser Gly Thr Leu His Val Pro Thr Met Gly Met Val
    210                 215                 220

Ala Leu Val Thr Ala Leu His Val Cys Gln Gly Val Thr Ile Thr Gly
225                 230                 235                 240

Phe Gly Tyr Pro Asn Gly Gly Pro Asn Gln Phe Ile His Tyr Tyr Asn
                245                 250                 255

Gly Tyr Thr Met Arg Ala Met Gln Asn Ser Ile His Asp Val Asn Ala
            260                 265                 270

Glu Lys Thr Ile Ile Glu Arg Met Ile Gln Asn Lys Thr Ile Leu Cys
        275                 280                 285

Ile Arg
    290


<210> SEQ ID NO 10
<211> LENGTH: 1806
<212> TYPE: DNA
<213> ORGANISM: Myxoma virus
<220> FEATURE:
<221> NAME/KEY: CDS
<222> LOCATION: (2)..(439)
<220> FEATURE:
<221> NAME/KEY: CDS
<222> LOCATION: (1405)..(1806)

<400> SEQUENCE: 10

g ttg cat aag gaa ctc ccc agt caa gat tgg ttt tct ttt tac gtg gaa      49
  Leu His Lys Glu Leu Pro Ser Gln Asp Trp Phe Ser Phe Tyr Val Glu
    1               5                  10                  15

gta ttc cac tgc tac act tcc gtg ata tac gcg gta gtt gac gga gcc        97
Val Phe His Cys Tyr Thr Ser Val Ile Tyr Ala Val Val Asp Gly Ala
            20                  25                  30

gtt cta tac gca aac gcc gat tac aaa aca cat tgt acg ata agc gat       145
Val Leu Tyr Ala Asn Ala Asp Tyr Lys Thr His Cys Thr Ile Ser Asp
        35                  40                  45
```

-continued

```
gac cga cga cat agg gaa gac gtt acg gac gat tgt ctg tgt tgt cac      193
Asp Arg Arg His Arg Glu Asp Val Thr Asp Asp Cys Leu Cys Cys His
     50                  55                  60

gta tct cct caa att cgt acg ttc ggt aca cag gta atg gag aac gta      241
Val Ser Pro Gln Ile Arg Thr Phe Gly Thr Gln Val Met Glu Asn Val
 65                  70                  75                  80

gag tgt cgg gtg gta cgg gat ggt tta tgt atc gaa ata aaa cac gtg      289
Glu Cys Arg Val Val Arg Asp Gly Leu Cys Ile Glu Ile Lys His Val
                 85                  90                  95

gga aaa ttc gga gca tcg tgc gta ggt gcg tat aat acg cgg tat ata      337
Gly Lys Phe Gly Ala Ser Cys Val Gly Ala Tyr Asn Thr Arg Tyr Ile
            100                 105                 110

aaa ata gcg ata ggg tcg gtg tac gat atc att cta aaa cag gac ggg      385
Lys Ile Ala Ile Gly Ser Val Tyr Asp Ile Ile Leu Lys Gln Asp Gly
        115                 120                 125

atg tcc gga aag aag cga cat agt tgc tac gtg tac gga atc gcc cga      433
Met Ser Gly Lys Lys Arg His Ser Cys Tyr Val Tyr Gly Ile Ala Arg
    130                 135                 140

cgg tag gcttgcgaaa tagtgtattg tttttatca gagttagcgt atacaaagga      489
Arg
145

tcgtcttatt ttggatcata cgttcgatga tcgttttctc cgcgtttacg tcgtgaatgg    549

agttttgcat ggcacgcata gtatagccgt tgtaataatg gataaattgg ttaggccccc    609

cattggggta cccgaatccc gtaatcgtta cgccctggca cacgtgtaac gcggtcacga    669

gcgcgaccat tcccatcgta ggaacgtgca acgttccgga cgttgtctgt atacgcaacg    729

ccgcatcgta cgtatatttc ggatgtagga ttcgtacgaa cgccggacgc gcgcgccacg    789

tgcgaggcgg tttcttccaa aatctagaca ggtcgacgcg tgcgttgttc gtaagcatgt    849

tatatagcca gtataagtcg gcggacttga acggaaccat tacaaacagc gtcgtattat    909

cgttttcttt cacggaatcc gattgggcgg attccgggta gaacatacgt atcgtcgttt    969

ttgtcccaac gtctcgttcg aaggcacgaa cgggagcgtc gtttaaccga aacaccacgt   1029

cgtacgagtc gatgattcgt cctaaagatc tattgtgtaa gttataacta tttcctacga   1089

cgatacattg tttgccgtat aagaggaaat taggaagatg tccaggaatc ttttctaaca   1149

gacgacgtat ctgcgcttcc tctcctttta gcccgtacgg taaacgtctt tcgaacgtat   1209

tattgtgggt tacaaatacg tttgtgacgg atacgttgtt cgttccgtgg tttaccacgg   1269

acattttcaa cgacattacg aacaacgcaa ctgcggtaca tgcgtacacc atcgtgcatc   1329

gtttaaagaa atacatatcg cagaagcaag atttttttg tgttttagtc tacccaacgt   1389

acgcgataga acact atg agc aac tac gta aag ttc gac gta tcg atc gaa   1440
                 Met Ser Asn Tyr Val Lys Phe Asp Val Ser Ile Glu
                             150                 155

gat gac tgt atc aat ata acg gtc agt aac act agt tta ccc atc cac     1488
Asp Asp Cys Ile Asn Ile Thr Val Ser Asn Thr Ser Leu Pro Ile His
    160                 165                 170

gta aag acc gtc ccc aaa cgc aca cat cgg gac aat tac gtg ttt aaa     1536
Val Lys Thr Val Pro Lys Arg Thr His Arg Asp Asn Tyr Val Phe Lys
175                 180                 185                 190

aac act ata gac gcc tcg gac gat atc gtc tct atc cta cac aac tat     1584
Asn Thr Ile Asp Ala Ser Asp Asp Ile Val Ser Ile Leu His Asn Tyr
                195                 200                 205

ata tgg tac aga gga ttt ata ggt ctg ccg aac aaa tac ggt agg gtg     1632
Ile Trp Tyr Arg Gly Phe Ile Gly Leu Pro Asn Lys Tyr Gly Arg Val
            210                 215                 220

ttc aaa gaa cta aag ctc ttc gac atc gac gca aag acc aaa tac gga     1680
```

-continued

```
Phe Lys Glu Leu Lys Leu Phe Asp Ile Asp Ala Lys Thr Lys Tyr Gly
        225                 230                 235

gat ata aat act tta ttt ttc atg tta aat tta aac tcg gat cgt tgc      1728
Asp Ile Asn Thr Leu Phe Phe Met Leu Asn Leu Asn Ser Asp Arg Cys
    240                 245                 250

tgc agg aat ttt tcc aat ttc gta aca cta caa aaa act ata ttc aaa      1776
Cys Arg Asn Phe Ser Asn Phe Val Thr Leu Gln Lys Thr Ile Phe Lys
255                 260                 265                 270

cac acg gtt acc gta tac aac tgc atc gaa                              1806
His Thr Val Thr Val Tyr Asn Cys Ile Glu
                275                 280


<210> SEQ ID NO 11
<211> LENGTH: 145
<212> TYPE: PRT
<213> ORGANISM: Myxoma virus

<400> SEQUENCE: 11

Leu His Lys Glu Leu Pro Ser Gln Asp Trp Phe Ser Phe Tyr Val Glu
  1               5                  10                  15

Val Phe His Cys Tyr Thr Ser Val Ile Tyr Ala Val Val Asp Gly Ala
             20                  25                  30

Val Leu Tyr Ala Asn Ala Asp Tyr Lys Thr His Cys Thr Ile Ser Asp
         35                  40                  45

Asp Arg Arg His Arg Glu Asp Val Thr Asp Asp Cys Leu Cys Cys His
     50                  55                  60

Val Ser Pro Gln Ile Arg Thr Phe Gly Thr Gln Val Met Glu Asn Val
 65                  70                  75                  80

Glu Cys Arg Val Val Arg Asp Gly Leu Cys Ile Glu Ile Lys His Val
                 85                  90                  95

Gly Lys Phe Gly Ala Ser Cys Val Gly Ala Tyr Asn Thr Arg Tyr Ile
            100                 105                 110

Lys Ile Ala Ile Gly Ser Val Tyr Asp Ile Ile Leu Lys Gln Asp Gly
        115                 120                 125

Met Ser Gly Lys Lys Arg His Ser Cys Tyr Val Tyr Gly Ile Ala Arg
    130                 135                 140

Arg
145


<210> SEQ ID NO 12
<211> LENGTH: 134
<212> TYPE: PRT
<213> ORGANISM: Myxoma virus

<400> SEQUENCE: 12

Met Ser Asn Tyr Val Lys Phe Asp Val Ser Ile Glu Asp Asp Cys Ile
  1               5                  10                  15

Asn Ile Thr Val Ser Asn Thr Ser Leu Pro Ile His Val Lys Thr Val
             20                  25                  30

Pro Lys Arg Thr His Arg Asp Asn Tyr Val Phe Lys Asn Thr Ile Asp
         35                  40                  45

Ala Ser Asp Asp Ile Val Ser Ile Leu His Asn Tyr Ile Trp Tyr Arg
     50                  55                  60

Gly Phe Ile Gly Leu Pro Asn Lys Tyr Gly Arg Val Phe Lys Glu Leu
 65                  70                  75                  80

Lys Leu Phe Asp Ile Asp Ala Lys Thr Lys Tyr Gly Asp Ile Asn Thr
                 85                  90                  95
```

-continued

```
Leu Phe Phe Met Leu Asn Leu Asn Ser Asp Arg Cys Cys Arg Asn Phe
            100                 105                 110

Ser Asn Phe Val Thr Leu Gln Lys Thr Ile Phe Lys His Thr Val Thr
        115                 120                 125

Val Tyr Asn Cys Ile Glu
    130


<210> SEQ ID NO 13
<211> LENGTH: 289
<212> TYPE: PRT
<213> ORGANISM: Myxoma virus

<400> SEQUENCE: 13

Met Tyr Phe Phe Lys Arg Cys Thr Met Val Tyr Ala Cys Thr Ala Val
  1               5                  10                  15

Ala Leu Phe Val Met Ser Leu Lys Met Ser Val Val Asn His Gly Thr
             20                  25                  30

Asn Asn Val Ser Val Thr Asn Val Phe Val Thr His Asn Asn Thr Phe
         35                  40                  45

Glu Arg Arg Leu Pro Tyr Gly Leu Lys Gly Glu Glu Ala Gln Ile Arg
     50                  55                  60

Arg Leu Glu Lys Ile Pro Gly His Leu Pro Asn Phe Leu Leu Tyr Gly
 65                  70                  75                  80

Lys Gln Cys Ile Val Val Gly Asn Ser Tyr Asn Leu His Asn Arg Ser
                 85                  90                  95

Leu Gly Arg Ile Ile Asp Ser Tyr Asp Val Val Phe Arg Leu Asn Asp
            100                 105                 110

Ala Pro Val Arg Ala Phe Glu Arg Asp Val Gly Thr Lys Thr Thr Ile
        115                 120                 125

Arg Met Phe Tyr Pro Glu Ser Ala Gln Ser Asp Ser Val Lys Glu Asn
    130                 135                 140

Asp Asn Thr Thr Leu Phe Val Met Val Pro Phe Lys Ser Ala Asp Leu
145                 150                 155                 160

Tyr Trp Leu Tyr Asn Met Leu Thr Asn Asn Ala Arg Val Asp Leu Ser
                165                 170                 175

Arg Phe Trp Lys Lys Pro Pro Arg Thr Trp Arg Ala Arg Pro Ala Phe
            180                 185                 190

Val Arg Ile Leu His Pro Lys Tyr Thr Tyr Asp Ala Ala Leu Arg Ile
        195                 200                 205

Gln Thr Thr Ser Gly Thr Leu His Val Pro Thr Met Gly Met Val Ala
    210                 215                 220

Leu Val Thr Ala Leu His Val Cys Gln Gly Val Thr Ile Thr Gly Phe
225                 230                 235                 240

Gly Tyr Pro Asn Gly Gly Pro Asn Gln Phe Ile His Tyr Tyr Asn Gly
                245                 250                 255

Tyr Thr Met Arg Ala Met Gln Asn Ser Ile His Asp Val Asn Ala Glu
            260                 265                 270

Lys Thr Ile Ile Glu Arg Met Ile Gln Asn Lys Thr Ile Leu Cys Ile
        275                 280                 285

Arg
```

METHOD OF PRODUCING α2,3-SIALYLTRANSFERASE

This invention relates to a method of producing α2,3 sialyltransferase.

This invention has particular but not exclusive application to production of an enzyme having eukaryotic α2,3-Galβ1,3(4) GlcNAc sialyltransferase activity, and for illustrative purposes reference will be made to such application. However, it is to be understood that this invention could be used in other applications, such as production of assays for enzymes having eukaryotic α2,3-Galβ1,3(4) GlcNAc sialyltransferase activity.

The glycosyltranferases are a highly polymorphic group of membrane-bound enzymes of endoplasmic reticulum and Golgi bodies that catalyze the transfer of a single monosaccharide unit from a nucleotide donor to the hydroxyl group of an acceptor saccharide in the biosynthesis of N-glycan (Asn-GlcNAc N-glycosidic linkage; GlcNAc, N-acetylglucosamine) and O-glycan (Ser/Thr-GalNAc, O-glycosidic linkage; GalNAc, N-acetylgalactosamine) moieties of glycoproteins and glycolipids.

The eukaryotic sialyltransferases comprise a family of glycosyltransferases that catalyze the transfer of N-acetylneuraminic acid (NeuAc), a sialic acid (SA), from CMP-SA to oligosaccharide chains of glycoconjugates. The addition of the SA normally terminates oligosaccharide chain elongation except for polysialic chains found on neural cell adhesion molecule and gangliosides.

Known eukaryotic sialyltransferases involved in the synthesis of N- and O-glycan derivatives of glycoprotein and glycolipid are summarized in Table 1, adapted from Palcic (1994 Methods in Enzymology, 230:300). In the table, the transferred sugar residue is in bold, and R represents the remainder of the acceptor glycoprotein, glycolipid or oligosaccharide chain.

TABLE 1

| Sialyltransferase (ST) | EC number | Linkage synthesised |
|---|---|---|
| Gal(2-6)-ST(ST6N) | 2.4.99.1 | NeuAcα2->6Galβ1->4GlcNAc-R |
| GalNAcα(2-6)-ST (ST6OI) | 2.4.99.4 | NeuAcα2->6GalNAcα-R |
| Gal(2-3)-ST(ST3O) | 2.4.99.4 | NeuAcα2->3Galβ1->4GalNAcα-R |
| Gal(2-3)-ST(ST3N) | 2.4.99.6 | NeuAcα2->3Galβ1->3/4GlcNAc-R |

GalNAcα(2-6)-ST(ST60II)2.4.99.7 NeuAcα2→3Galβ1→3GalNAc-R N-Ac-neuramide α(2-8)-2.4.99.8 NeuAcα2→8NeuAcα2→Galβ-R sialyltransferase Proteins produced by prokaryotes rarely possess N-terminal sugar chains, whereas eukaryotes exhibit many examples of such glycoproteins. α2,3-sialyltransferases are useful eukaryotic enzymes for in vitro synthesis of N-linked and O-linked sialyl derivatives of glycoproteins, for determinations of acceptors, and other qualitative and quantitative research of glycoproteins.

Only three glycosyltransferases are commercially available. These are the β1,4-galactosyltransferase (EC 2.4.1.38/2.4.1.90) isolated from bovine and human milk, the α2,6 Galβ1,4 GlcNAc-sialyltransferase (ST6N, EC 2.4.99.1) isolated from rat liver, and the α2,3 Galβ1,3 GalNAc-sialyltrasferase (ST30, EC 2.4.99.4) isolated from porcine liver. The ST30 enzyme has been withdrawn from the market by its erstwhile suppliers. No commercial source of α2,3 Galβ1,3(4) GalNAc-sialyltrasferase (ST3N) or other glycosyltransferases currently exist.

No high expression vectors for cloned transferases are widely available, and accordingly most researchers isolate the required glycosyltransferases from mammalian tissues. Isolations from mammalian tissues are complicated by the low natural abundance of the glycosyltransferases and the need for chromatography for partial purification. These factors combine to render the isolates prone to contamination with other glycosyltransferases as well as enzyme inhibitors, resulting in poor and inconsistent results.

A method for partial purification of ST3N from rat liver is described by Palicic (1994, Methods in Enzymology 230:300) following the procedure of Weistein et al (1982, J.Biol.Chem. 257:13835). However, this process requires the use of animals as the source of the tissues and therefore adds to the number of animals sacrificed. Ethical considerations oblige researchers to seek and use procedures and processes that do not require animals where that is possible.

In another approach to production of enzymes having α2,3-sialyltransferase activity, U.S. Pat. No. 5,384,249 (Sasaki, et al.) discloses a method comprising isolation of cDNA coding for enzyme having the activity of an α2,3-sialyltransferase from a cDNA library constructed from mRNA of human cell lines TYH (human histiocytic leukemia cell line) or WM266 (human melanoma cell line), insertion into an expression cloning vector and selection against a lectin medium. The selected clones are isolated, amplified and target DNA isolated from the vector. After coupling to a suitable promoter, the cDNA isolate is used to transform a suitable prokaryote or eukaryote host cell for expression.

The process of the disclosed method is of course a complex one and in keeping with many like processes the efficiency of expression of the inserted exogeneous DNA may vary over time. Further, inhibition may preclude commercially useful expression of the enzyme exhibiting α2,3-sialyltransferase activity.

The present invention aims to substantially alleviate at least one of the above disadvantages and to provide a method for the preparation of α2,3-sialyltransferase which will be reliable and efficient in use. Other objects and advantages of this invention will hereinafter become apparent.

With the foregoing and other objects in view, this invention in one aspect resides broadly in a method of preparation of lysates having α2,3-sialyltransferase activity including the steps of:

infecting a cell culture having essentially no endogenous expression of eukaryotic α2,3-sialyltransferase with a poxviral agent including a gene expressing on infection a protein having eukaryotic α2,3-sialyltransferase activity, and a promoter therefor, and harvesting a lysate of said infected cell culture containing a protein having α2,3-sialyltransferase activity.

In a further aspect this invention resides broadly in compositions having in vitro α2,3-sialyltransferase activity and comprising a protein extract of lysates of a eukaryote cell culture, having essentially no endogenous expression of eukaryotic α2,3-sialyltransferase, cultured with a poxviral agent including a gene and promoter expressing in said culture a protein having eukaryotic α2,3-sialyltransferase activity.

The applicant has unexpectedly determined that certain poxviral genomes include genes coding for proteins having eukaryotic α2,3-sialyltransferase activity, which are expressed in infected substrates to a commercially useful degree. Especially, it has been determined by the applicant that Leporipoxvirus including the Brazilian myxoma virus (MYXV), Shope (rabbit) fibroma virus, hare fibroma virus, squirrel fibroma virus and Californian myxoma virus.

MYXV naturally infects the Brazilian tapeti (*Sylvilagus brasiliensis*) and causes the development of a small localised tumour which persists for several months and then regresses rapidly. In contrast to the trivial symptoms in its natural host, infection of the European rabbit (*Oryctolagus cuniculus*) with MYXV causes the devastating disease myxomatosis.

Preferably the poxvirus is selected from the myxoma viruses of rabbits including a wild type endogenous gene and promoter coding for a eukaryotic α2,3-sialyltransferase. However, it is envisaged that sialyltransferase gene encoded by myxoma virus may not be unique to this virus and could be encoded by other poxviruses of the Leporipoxvirus genus.

Related sialyltransferase genes could also be encoded by other genera of the sub-families Chordopoxvirinae, Entomopoxvirinae and unclassified viruses of the family Poxviridae (Esposito 1991, Archives of Virology (Suppl) 2:91). Examples of potential candidate poxviruses are given in Table 2.

TABLE 2

Family: Poxviridae; Subfamily: Chordopoxviridae

| Genus | Prototype virus |
|---|---|
| Orthopoxvirus | vaccinia virus |
| Parapoxvirus | orf virus |
| Capripoxvirus | sheep pox virus |
| Suipoxvirus | swinepox virus |
| Leporipoxvirus | myxoma virus |
| Avipoxvirus | fowlpox virus |
| Yatapoxvirus | yaba monkey tumour virus |
| Molluscipoxvirus | molluscum contagiosum virus |

Sialyltransferase assays of poxvirus infected cell lysates, as described in this application, may be used to determine if the individual poxvirus species express an active sialyltransferase enzyme. These assays may be conducted by observing the transfer of a labelled sialic acid from CMP-SA to a glycoconjugate acceptor. Such labelled donors may be CMP-[$H^3$]SA, CMP-[$C^{14}$]SA or CMP-9 fluoresceinyl-SA (Gross et al, 1990, Analytical Biochem, 186:127). The labelled acceptors may be visualised by SDS-PAGE or thin layer chromatography followed by autoradiography or fluorography. Alternatively when using CMP-9-fluoresceinyl-SA the labelled acceptor may be separated by from donor molecules by Sephadex G-50 fine chromatography and the extent of labelling of the acceptor measured using a florescence spectrophotometer (fluorometer).

Other poxviruses may contain a related sialyltransferase gene located in the same genomic location as the myxoma virus Uriarra and Lausanne strains, ie between the genes equivalent to A51 and A52 of the Copenhagen strain of vaccinia virus (Goebel et al, 1990, Virology 179:247). These related sialyltransferase genes could be isolated by polymerase chain reaction using appropriate primers.

Accordingly, in a further aspect, this invention resides in the set of degenerate primers: [SEQ ID NOS:192]

CAP-I

GGGATCCAT[A/T/C]TC[T/C]AG[A/G]CA[T/C]AA[A/G]CG

CAP-11 GGGATCCGC[A/G]CA[T/C]AA[A/T/C/G]CC[T/G/A]ATCAT

These primers have been designed based on conserved amino acids between the variola and myxoma viruses. CAP-I is located within the A51 gene corresponding to the translation I-S-R-H-K-R. CAP-II is complementary to the A52 gene sequence corresponding to the translation M-I-G-L-C-A. Amplification of poxvirus DNA using these primers should generate a product of 0.9 kb for viruses which do not encode additional DNA between A51 and A52 (no sialyltransferase gene at this genomic location), and 1.9 kb or larger for viruses which contain addition DNA sequence between the A51 and A52 genes. For the myxoma viruses, 1.9 kb, the addition of 1 kb of DNA corresponds to the sialyltransferase gene.

Vaccinia virus contains a conservative substitution within primer site CAP-I with Q codon instead the K codon of variola and myxoma viruses. This results in a mismatch at position 20 to the oligonucleotide CAP-I. Nevertheless under the amplification conditions a major 0.9 kb product was generated using a vaccinia virus, strain wr, DNA template. Indicating that the primers can tolerate minor mismatch during the amplification procedure.

Myxoma virus is known to replicated in a number of permissive cultured cells of rabbit, chicken, squirrel, hamster, monkey and guinea pig (McFadden, 1988, In "Virus diseases in laboratory and captive animals." Ed. G Darai. Martinus Nijhoff Publishing, Boston. pp36–62). This laboratory has successfully cultured myxoma virus on RK13 (ATCC CLL-37), SIRC (ATCC CLL-60), CV1 (ATCC CLL-70) and VERO (ATCC CLL-81) cells. Attempts to generate productive infection of Human 143B (ATCC CRL-8303), L-M (TK-) (ATCC CLL-1.3) or BHK-21 tk-ts13 (ATCC CRL-1632) were unsuccessful indicating they are non-permissive for viral replication.

Studies have shown that infection of non-permissive culture cells with poxvirus can result in a block to virus DNA replication and thus late gene transcription and viral morphogenesis. Under these circumstances there is no switch from early to intermediate/late gene transcription therefore early genes continue to be transcribed and expressed resulting in an amplification of viral early proteins.

Accordingly, in a further aspect this invention resides in a method for producing myxoma virus sialyltransferase comprising harvesting viral early proteins amplified in a cell line non-permissive for viral replication, and isolating said myxoma virus sialyltransferase.

The myxoma virus sialyltransferase gene is transcribed during the early phase of infection, therefore infection of one of the above described non-permissive cell lines may result in an amplified sialyltransferase activity in the triton cell lysates compared to permissive cell viral infection.

Accordingly, cell cultures may be selected from those permissive for infection by myxoma, such as rabbit cells per se having essentially no endogenous expression of eukaryotic α2,3-sialyltransferase. However, it is envisaged that circumstances may provide for the use of other cell cultures such as the African green monkey cell line CV1 (ATCC CCL70), permissive for the virus and further permissive as a negative control with Vaccinia virus. Additionally, it is envisaged that certain non permissive cell lines may be useful where the early-expression sialyltransferase product is produced on infection prior to inhibition of the virus.

As used herein, the expression "having essentially no endogenous expression of eukaryotic α2,3-sialyltransferase" should be taken to means that the enzyme if produced endogenously in the selected cells occurs in such minute quantities that expression of the product enzyme of the invention effectively masks all detection. Additionally, it is preferred that the cells are selected for essentially no endogenous expression of other sialyltransferases.

It has been surprisingly determined that commercially useful titres of a polypeptide having α2,3-sialyltransferase activity are obtained in lysates of in vitro infection and culture of cells, having little or no endogenous sialyltransferase expression, with myxoma virus. This unexpected result appears not to be subject to cellular inhibition, and the lysates are statistically substantially pure with respect to the target α2,3-sialyltransferase as opposed to competing enzymes of differing specificity such as cellularly mediated 2,6 sialyltransferases. Conventional wisdom would have it that the cultured cells should be those having endogenous expression of the enzyme, such as liver cells.

Figure 2:
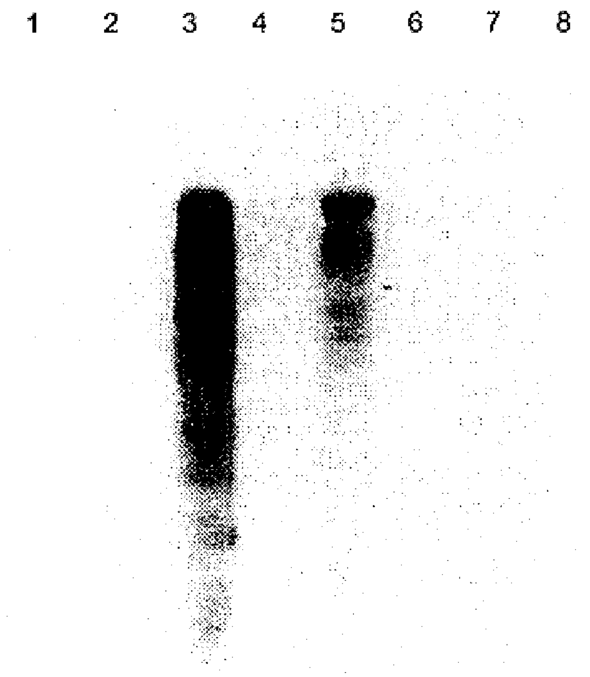

In order that this invention may be more readily understood and put into practical effect, reference will now be made to the accompanying examples and sequence listings which illustrate a preferred embodiment of the invention, described with reference to FIGS. 1 to 5, wherein:

FIG. 1 comprises the EcoRI restriction map of the myxoma virus genome, illustrating above the map the location of the sialyltranferase gene (MST3N);

FIG. 2 is a fluorograph showing $^3$H-labelled sialylated fetuin following sialyltransferase and PNGaseF reactions, wherein the lysates correspond to lanes: 1) Vaccinia virus; 2) as 1+PNGaseF; 3) vaccinia virus+5 mUnits ST6N; 4) as 3+PNGaseF; 5) myxoma virus; 6) as 5+PNGaseF; 7) Lu (MST3N$^-$/lacZ$^+$); 8) as 7+PNGaseF.

Figure 3:
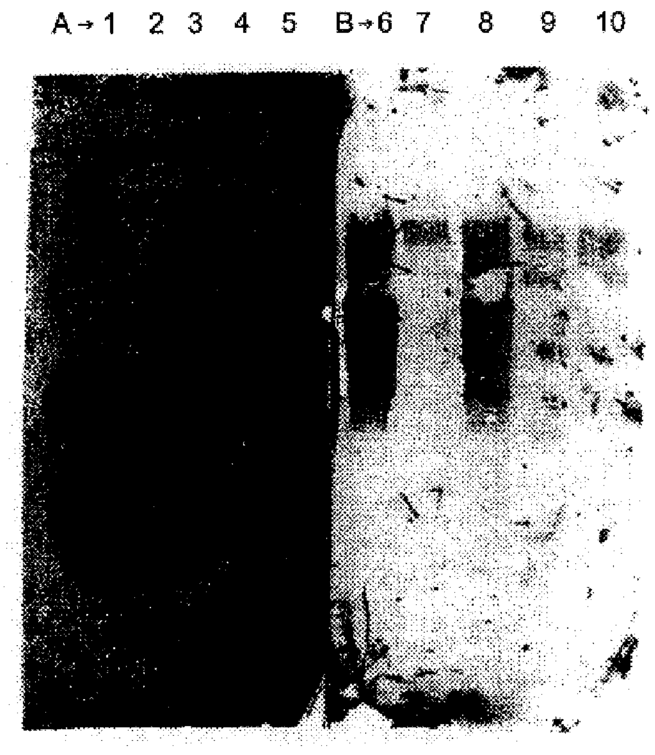
Figure 4:
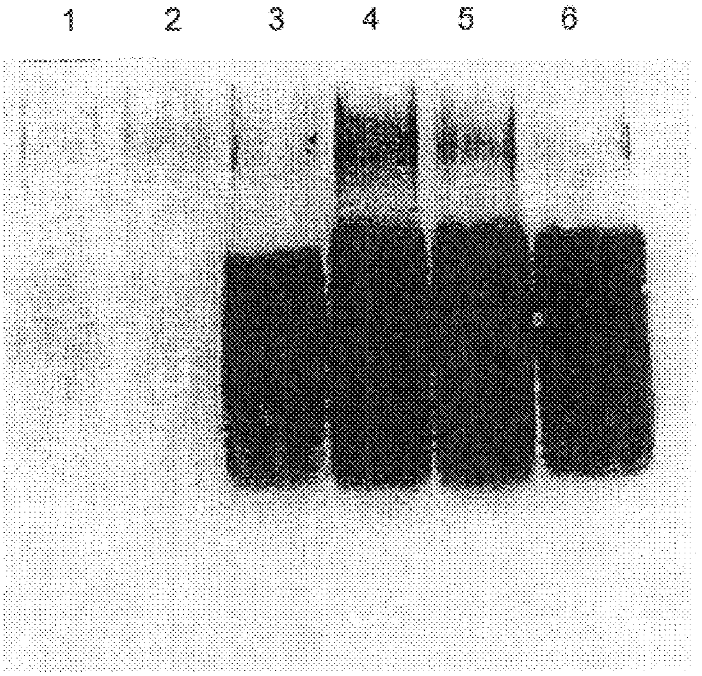
Figure 5:
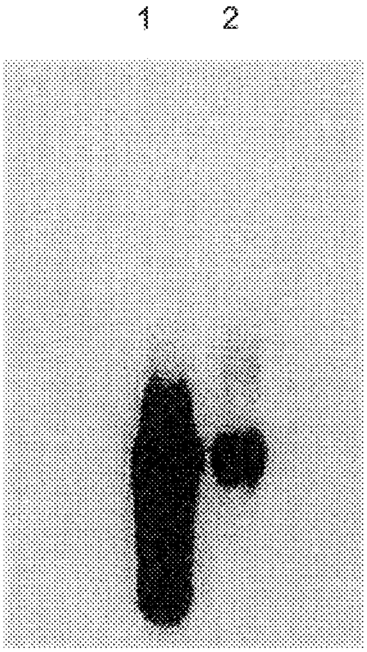

FIG. 3 comprises lectin binding assays wherein: Lanes 1 & 6. MYXV+CMP-SA; Lanes 2 & 7 MYXV; Lanes 3 & 8 VACV+CMP-SA+ST6N; lane 4 & 9 VACV+CMP-SA; lane 5 & 10 VACV. A) lectin SNA-DIG & B) lectin MAA-DIG;

FIG. 4 shows lectin binding assay using MAA-DIG to extracts of poxvirus infected RK13 cells, wherein lanes are: 1) VACV+ST6N; 2) VACV; 3) SFV; 4) MSD; 5) MSW; 6) Lu, and FIG. 5 comprises the Northern blot of myxoma virus Lu RNA.

Sequence 1 [SEQ ID NO:3] comprises Myxoma virus MA51 [SEQ ID NO:4] and protein kinase (MB1) [SEQ ID NO:8] genes, partial cds, alpha-2,3-sialyltransferase (MST3N) [SEQ ID NO:9], (MA52) [SEQ ID NO:5, (MA55) [SEQ ID NO:6] and (MA56) [SEQ ID NO:7] genes, and Sequence 2 [SEQ ID NO:10] comprises Myxoma virus (MA51) [SEQ ID NO:11] and (MA52) [SEQ ID NO:12] genes, partial cds, alpha-2,3-sialyltransferase (MST3N) [SEQ ID NO:13] gene, complete cds.

EXAMPLE 1

Myxoma virus genomic restriction mapping and subcloning studies were conducted by Russell and published in Russell & Robbins (1989) *Virology* 170:147. The myxoma virus DNA contained within the clones was not characterised at either the nucleotide or genetic level, but have been a major source of myxoma virus material for the development of the present invention. The myxoma virus DNA clone used in this invention was derived from a laboratory derivative of the Uriarra strain, (Mykytowycz, (1953) Nature 172:448; Russell & Robbins, 1989) which is an Australian field derivative of the Standard Laboratory Strain (SLS, ATCC VR-116), itself derived from the Moses strain, which was released in Australia in 1950.

The myxoma virus, strain Uriarra, EcoRI-G2 fragment was obtained from pUrE-G2 (Russel & Robbins, 1989) and subcloned into pGem7Z(f−) (Promega Corporation). The SalI-R2 fragment contained within the EcoRI-G2 DNA fragment was subcloned into pGem3Z(f+) (Promege Corporation) and a partial DNA sequence determined. The DNA sequence determined contained a "unique" poxvirus gene/protein which when used to scan the GENBANK database using the BLASTp program with default parameters contained similarity to the human "CD75 antigen". The human gene was later found to actually encode an α2,6-sialyltransferase (ST6N) which is responsible for formation of the sialic acid-containing CD75 antigen. (Stamenkovic et al.,1990, J.Exp.Med. 172:641; Bast et al.,1992, J.Cell.Biol. 116:423)

The DNA sequence of the larger region of the EcoRI-G2 myxoma virus fragment which corresponds to the BamHI-N fragment plus the DNA sequence to the right-hand end of the EcoRI-G2 fragment was determined. The myxoma virus genes encoded by this region are MA51 (partial sequence), MA51a (MST; α2,3-sialyltransferase), MA52, MA55, MA56 (orthopoxvirus haemagglutinin related) and MB1 (serine/threonine kinase related). Five of these genes show nucleotide similarity to vaccinia virus, strain Copenhagen, genes A51 through B1 (Goebal et al, 1990 *Virology* 179:247), the sixth gene, MST3N, being a newly identified poxvirus gene showing similarity to eukaryotic sialyltransferases.

Transcription analysis of the wild type Lausanne strain (Lu;ATCC VR-115: Bouvier, 1954, Bulletin de l'Office International des Epizooites 46:76) MST3N gene was conducted essentially as described in Jackson & Bults, (1992, J Gen. Virol. 73:3241). Both myxoma virus early and late polyadenylated mRNA preparations were hybridized to a $P^{32}$-labelled strand specific RNA probe for the MST gene. The autoradiograph was developed and demonstrated that the MST gene is transcribed early in infection giving a major transcript of approximately 1100 nucleotides. It appears that either the major MST early MRNA persists late in infection or transcription of the early promoter is re-initiated during late infection as significant levels of MST early sized transcripts were still present during late phase of infection.

A recombinant myxoma virus, Lu(MST-,LacZ$^+$), was constructed using wild-type Lausanne strain, with the MST gene disrupted by insertion of the *E.coli* lacZ gene into the region encoding the sialyl motif. This recombinant virus was constructed to demonstrate that the MST3N gene encoded a protein responsible for the sialyltransferase activity observed in cell lysates of wild-type virus.

Triton detergent lysates of tissue culture cells infected with either vaccinia virus (strain wr;ATCC VR-119), myxoma virus (strain Lu) or Lu (MST-,lacZ$^+$), were prepared and used in in vitro sialyltransferase reactions. These experiments demonstrated that the myxoma virus infected cells contained an easily detectable sialyltransferase active which transferred [$H^3$]—labelled sialic acid to the asialylated acceptor glycoprotein as determined by SDS-PAGE and fluorography using an overnight exposure. Vaccinia virus infected cells treated in an identical manner do not show detectable sialyltransferase activity. The myxoma virus sialyltransferase activity was abolished when the MST gene is disrupted, Lu (MST-,lacZ$^+$), demonstrating that the identified MST gene encodes a protein with sialyltransferase activity. These experiments also demonstrated that endogenous cellular sialyltransferase activity was below detection limits on overnight exposure of the fluorographs although very weak signals could be detected on extended exposure (4 days). The experiments with the MST-recombinant myxoma virus also demonstrates that infection with myxoma virus does not induce increased cellular sialyltransferase activity.

The nature of the myxoma virus sialyltransferase directed oligosaccharide linkage (O or N linked) to the glycoprotein acceptor was determined by treatment of the myxoma virus sialyltransferase [H3]-SA labelled glycoprotein acceptor with PNGase-F, which removes N-linked oligosaccharide from protein substrates. Using this glycosidase all the [$H^3$]-labelled sialic acid was N-linked but not O-linked, as illustrated in FIG. 2, wherein lane 1 and 2 are vaccinia virus strain wr cell lysate, lanes 3 and 4 are vaccinia virus wr infected cell lysate plus 5 mUnits of α2,6-sialyltransferase (ST6N), lanes 5 and 6 are myxoma virus Lu infected cell lysate, and lanes 7 and 8 are recombinant myxoma virus Lu(MST-,lac$Z^+$) infected cell lysate. Lanes 2, 4, 6 and 8 also included 0.4 units of N-glycosidase-F.

The nature of the type of sialic acid linkage (α2,3 or α2,6) was determined by saturation labelling of asialylated glycoprotein acceptor with "cold" sialic acid using the myxoma virus cell extract and determining the type of linkage using digoxigenin labelled lectin binding assay, as per FIG. 3, wherein:

Lanes 1 and 6: myxoma virus Lu infected cell lysate plus CMP-SA

Lanes 2 and 7: myxoma virus Lu infected cell lysate without CMP-SA

Lanes 3 and 8: vaccinia virus wr strain infected cell lysate plus 5 mUnits of α2,6-sialyltransferase (ST6N) plus CMP-SA Lanes 4 and 9: vaccinia virus wr strain infected cell lysate plus CMP-SA Lanes 5 and 10: vaccinia virus wr strain infected cell lysate without CMP-SA.

Lanes 1 to 5 were treated with the lectin probe Sambucus nigra agglutinin (SNA), specific for α2,6 linked SA, while lanes 6 to 10 were probed with Maackia amurensis agglutinin (MAA) specific for α2,3 linked SA. This demonstrated that the myxoma virus sialyltransferase specifically generates an α2,3 linkage to the glycoprotein acceptor.

The above results taken with the amino acid similarity to known sialyltransferases indicates that the MST3N gene encodes an active α2,3 Galβ1,3(4) GlcNAc-R sialyltransferase with a specificity for N-linked glycoprotein (ST3N; EC:2.4.99.6).

A) Identification of Myxoma Virus Sialyltransferase Gene DNA Sequencing and Plasmid Construction The myxoma virus 7.3 kb EcoRI-G2 DNA fragment located approximately 130 Kb from the left end of viral genome (FIG. 1) was sub-cloned in both orientations into pGem7Z(f−). A 4.7 kb of the DNA sequence was determined which corresponds to the right-end of the EcoRI-G2 fragment (see sequence listings).

The DNA sequence contains six open reading frames, five ORFs correspond to gene homologues (A51, A52, A55, A56 & B1) found in vaccinia virus (an Orthopoxvirus) and the sixth ORF, MST3N, shares similarity to known sialyltransferases (table 3).

The MYXV SalI-R2 fragment was ligated into the SalI site of pGem3Z(f+), generating pUrS-R2. The MYXV DNA fragment contained in pUrS-R2 was removed by digestion with EcoRI and HindIII and ligated between the respective sites of the transient dominant selection vector pGP7.5 gpt, generating pUrST1. The MST3N gene sequences contained in pUrST1 were interrupted by the insertion into the unique BglII site, a cassette.

B) Characterisation of the Sialyltransferase Activity Cells

SIRC (European rabbit (*Oryctolagus cuniculus*) cornea, ATCC CCL-60), RK13 (*O. cuniculus* kidney, ATCC CCL-37) and CV-1 (African Green Monkey (*Ceropithecus aethiops*) kidney, ATCC CCL-70) were maintained in Minimal Essential Medium (MEM) supplemented with 5% (v/v) foetal bovine serum (FBS).

Viruses a) Brazilian MYXV strains, Lausanne (Lu) (ATCC VR-115) isolated Campinas, Brazil, 1949 and Uriarra (Ur) isolated Australian Capital Territory, 1953 and is therefore a derivative of the Moses strain (ATCC VR-116) isolated São Paulo, Brazil 1909.

b) Vaccinia virus (VACV) strain wr (ATCC VR-1354).

c) Recombinant myxoma virus Lu (MST3$N^-$/lac$Z^+$) was constructed by liposome mediated transfection of Lu infected SIRC cells with pUrST1-lacZ and isolated using the transient dominant selection procedure as described previously.

Triton Cell Lysate Preparation

Confluent monolayers of CV1 cells were infected with poxvirus at an M.O.I of 1, in 80 $cm^2$ culture flasks. Twenty-four hours post-infection the cells were detached with PBS-EDTA at 37° C. and washed three times using PBS at 4° C. Cell lysates were prepared by suspension in 1 ml per flask of 50 mM MES-OH, pH 6.1; 0.5% (v/v) Triton-X100; 100 mM NaCl; 1.5 mM $MgCl_2$; 0.1 mM PMSF; 10 μg/ml aprotinin and incubation at 4° C. for 45 minutes. The lysate was clarified by centrifugation at 1750 g at 4° C. for 15 minutes. Supernatants were stored at −70° C. Total protein concentrations were measured using the BCA Protein Assay Reagent (Pierce).

Sialyltransferase Reactions

Cell lysates, 30 μl (containing 50 μg total protein), were mixed with 5 μl of asialofetuin (Sigma Type-I; 10 mg/ml in MES buffer [50 mM MES-OH, pH6.1; 0.5% (v/v) Triton X-100]) and 5 μl CMP-[$^3$H]-SA (DuPont NEN; dried and dissolved in MES buffer at 1 μCi/μl) and incubated for 90 minutes at 37° C. Reactions were terminated by heating at 90° C. for 10 minutes. An assay containing a vaccinia virus infected cell lysate sample was used as a negative control. A positive control consisted of the vaccinia virus infected cell lysate including 5 mUnits of α2,6-sialyltransferase (ST6N;EC:2.4.99.1; Boehringer-Mannheim).

PNGase-F Digestion

The total protein from the sialyltransferase reactions were precipitated using 8 volumes of acetone at −20° C. overnight and recovered by centrifugation for 30 minutes using a microcentrifuge. Protein pellets were air dried and resuspended in 10 μl of $H_2O$. The samples were denatured by the addition of 25 μl 0.1 M 2-Mercaptoethanol/0.5% (w/v) SDS and heated at 100° C. for 5 minutes. Samples were cooled to room temperature and the total volume adjusted to 40 μl with $H_2O$. Denatured protein aliquotes of 5 μl were mixed with 5 μl PNGase-F buffer (2X) [40 mM sodium phosphate buffer, pH 7.2; 20 mM EDTA; 3% (w/v) CHAPS]. Reactions were initiated by the addition of 0.4 Units N-Glycosidase F (Boehringer-Mannheim) and incubated at 30° C. for 16 hours. The reactions were terminated by heating at 100° C. for 5 minutes.

Polyacrylamide Gel Electrophoresis and Fluorography

Samples containing approximately 6 μg of the acceptor glycoprotein were separated by SDS-PAGE, fixed and stained within the gel. Flurographic detection of the labelled sialoglycoproteins (FIG. 2) was achieved by impregnating the stained gels with Amplify (Amersham) drying at 80° C. and exposure for 24 to 48 hours to pre-flashed Hyperfilm-MP (Amersham).

Determination of Sialoglycoprotein by Lectin Binding

For total "cold" sialylation of acceptor glycoprotein, triton lysates of viral infected cells (30 μl) were mixed with 5 μl of asialofetuin (10 mg/ml) with/without 10 μl of CMP-SA (10 mM; Sigma) and incubated at 37° C. for 24 hours. Glycoprotein samples (12 μg acceptor glycoprotein)

were separated by SDS-PAGE and electrophoretically transferred to PVDF membrane. Determination of the bound SA linkage to glycoprotein acceptor was accomplished using the DIG Glycan Differentiation Kit (Boehringer-Mannheim), using DIG labelled lectins, *Sambucus nigra* agglutinin (SNA; for 2,6 linked SA) and *Maackia amurensis* agglutinin (MAA; for 2,3 linked SA) as recommended by the manufacturer (FIG. 3).

Sialyltransferase activity of other leporipoxviruses (Californian myxoma viruses MSW San Francisco; MSD San Diago; SFV-OA Shope Fibroma virus Origional A strain) were analysed using the lectin binding assay as described above. All viruses express a similar sialyltransferase activity to Brazilian myxoma virus (FIG. 4), indicating that expression of an active "2,3 sialyltransferase is representative of the genus.

c) Determination of Time of Maximal Sialyltransferase Expression

Confluent (25 $cm^2$) RK13 cells were infected at an multiplicity of infection (MOI) of 5 with MYXV strain Lu and incubated at 33° C. At 10, 17 24 and 48 hours post infection, triton cell extracts (300 $\mu$l) were prepared as described above. Sialyltransferase activity (using fluorescence assay below) appears to be maximal between 24 and 48 hours post infection and coincides with maximal cytopathic effect (data not shown).

Sialyltransferase assays were performed using CMP-9-fluoresceinyl-SA (Boehringer Mannheim) as donor in 20 $\mu$l buffer (50 mM MES pH6.1; 0.1% Triton X-100 containing CMP-9-fluresceinyl-SA, 20 $\mu$M; acceptor glycoproten asialofetuin (Sigma) 1.5 mg/ml) at 37° C. for 15 minutes. Reaction were terminated by the addition of 4 $\mu$l of 0.1 M CTP. Labelled acceptor glycoprotein was separated from unincorporated donor by Sepadex G-50 gel filtration (NICK Spin columns; Pharmacia) using 0.1 M Tris pH8.6 as elution buffer. The extent of labelling of glycoprotein was determined using a CytoFluor II Fluorescence Reader (PerSeptive Biosystems) and 96 well plates.

d) Estimation of Sialyltransferase Activity

Ten 180 $cm^2$ flasks of confluent RK13 cells were infected at a MOI of 5 with Lu and harvested at 24 hrs PI when 100% CPE was evident. A triton cell extract (total 20 ml containing 3.1 mg total protein/ml isolated from 1.83 g of wet cells) were prepared as described above and used for a fluorescence sialyltransferase assay. A commercially available sialyltransferase ($\alpha$2,6-sialyltransferase EC:2.4.99.1 Boehringer Mannheim 83361420-Jul. 31, 1997) was used as a control to determine relative sialyltransferase activity.

Relative Sialyltransferase Activities:

Samples (10 $\mu$l) were used in reactions standardised to include 25 $\mu$g of total protein (RK13 cell lysate) in a 25 $\mu$l volume.

Raw Data [CytoFluor II Fluorescence Reader (PerSeptive Biosystems)]

Excitation 485: Emission 530: Gain 51

Data analysed and concentrations determined using Microplate

Manager II (V3.0) (BioRad)

Sample: Cytofluor reading

Blanks: 74 average

ST6N standards: 8 U/mg enzyme activity at 37° C. with CMP-N-acteylneuramic acid as substrate (approx. 2.5 U/mg enzyme at 37° C. with CMP-9(3-fluresceinyl-thioureido)-9-deoxy-N-acteyl-neuraminic acid as donor): units below are predicted activities of diluted enzyme relative towards CMP-SA.

100 $\mu$units: 1231/1140

50 $\mu$Units: 583/537

25 $\mu$Units: 309/283

Unknowns

Uninfected RK13 cells 10 $\mu$l neat sample (25 $\mu$g protein): 99/86=0.9 $\mu$Units sialyltransferase MYXV infected RK13 cells 10 $\mu$l of 1:10 dilution ( 3.17 $\mu$g protein) no glycoprotein acceptor: 111/103( activity to wards endogenous acceptors in RK13 lysate).

MYXV infected RK13 cells 10 $\mu$l samples

1:10 dilution (3.17 $\mu$g protein): 1332/1141=105.7 $\mu$Units sialyltransferase 1:20 dilution (1.59 $\mu$g protein): 777/749=65.4 $\mu$units sialyltransferase Relative Specific Activities RK13 cells: 0.9 $\mu$Units/25 $\mu$g=0.036 mU/mg total protein (probably an over estimate)

MYXV infected RK13 cells 65.4 $\mu$Units/1.6 $\mu$g=40.9 mU/mg total protein

Total sialyltransferase activity in 20 ml lysate contains 2.596 Units in 63.48 mg total protein isolated from 1.83 g of wet cells. Weinstein estimated that a rat liver (3.2 kg starting material) triton extract (20.8 liters; 68.5 g total protein) contained 9.9 units (specific activity 0.145 mUnits/mg) of $\alpha$2,3-sialyltransferase (EC:2.4.99.6).

Conclusion

The myxoma virus and other members of the Leporipoxvirus genus encode a gene which belongs to the sialyltransferase family (ie it contains a sialyl motif CMP-SA binding site) being most closely related to the $\alpha$2,3 Gal$\beta$1-3(4) GlcNAc sialyltransferase (EC:2.4.99.6). The myxoma virus MST3N gene encodes a protein of predicted MW of 33.3 kDa (non-glycosylated) being one of the smallest known sialyltransferase proteins. Basic characterisation of the sialyltransferase activity indicates that the enzyme has an $\alpha$2,3 sialyltransferase activity towards N-glycan of glycoproteins suggesting an $\alpha$2,3 Gal$\beta$1,3(4) GlcNAc sialyltransferase activity. Activity towards glycolipid acceptors has not been tested. Tissue culture cells infected with myxoma virus produce significant amounts of sialyltransferase activity by 24 hours post infection producing approximately a 280-fold specific activity than estimated can be obtained from rat the normal source of enzyme isolation. The relatively high level of expression and absence of other detectable sialyltransferase activities enables convenient purification by affinity chromatography using Cibacron Blue F3GA-Sepharoseand/or CDP-agarose.

EXAMPLE 2

Identification of candidate Poxvirus was undertaken using the set of degenerate primers: [SEQ ID NOS:1 & 2]

CAP-I GGGATCCAT[A/T/C]TC[T/C]AG[A/G]CA[T/C]AA[A/G]CG

CAP-II GGGATCCGC[A/G]CA[T/C]AA[A/T/C/G]CC[T/G/A]ATCAT

PCR-Reaction using Pfu polymerase (Stratagene) in 100 $\mu$l total volume

Poxvirus DNA (approximately 5 ng)

1×Pfu polymerase buffer (Stratagene)

CAP-I 1 $\mu$M

CAP-II 1 $\mu$M

NTP mixture 100 $\mu$M each

Pfu polymerase 2.5 Units (Stratagene)

30 cycles

94° C., 20 seconds

45° C., 1 minute

72° C., 30 seconds final extension at 72° C. for 5 minutes

EXAMPLE 3

Scale-up and Purification of the Myxoma Virus Sialyltransferase

Stocks of myxoma virus, Lu, can be prepared on RK13 cells to titres of approximately $10^7$ pfu/ml. If necessary concentrated viral stocks ($10^8$–$10^9$ pfu/ml) can be prepared by ultra-centrifugation of virus and re-suspension in an appropriate volume. Confluent roller bottle cultures of the most optimum cell type for sialyltransferase expression can be infected at a multiplicity of infection (MOI) of 1 or greater. Twenty-four to 48 hours post infection the cells can be harvested, washed in PBS and lysed using a Triton-MES buffer as described in the invention.

Affinity purification and concentration of the sialyltransferase may be performed by any suitable means known to the art, and in the present example by using a combination of CIBACRON BLUE 3GA-Sepharose 6B (Sticher et al, 1988, Biochem J 253:577) and CDP-Sepharose (Paulson et al, 1977, J Biol Chem, 252:2356) affinity chromatography.

It will of course be realised that while the above has been given by way of illustrative example of this invention, all such and other modifications and variations thereto as would be apparent to persons skilled in the art are deemed to fall within the broad scope and ambit of this invention as defined in the claims appended hereto.

What is claimed is:

1. A method of preparation of lysates having α2,3-sialyltransferase activity including the steps of:

infecting a cell culture having essentially no endogenous expression of eukaryotic α2,3-sialyltransferase with a poxviral agent having a poxviral α2,3-sialyltransferase gene, and a promoter therefor, and harvesting a lysate of said infected cell culture containing a protein having α2,3-sialyltransferase activity.

2. The method in accordance with claim 1, wherein said poxviral alpha 2,3-sialyltransferase is a myxoma virus sialyltransferase, further comprising harvesting viral early proteins amplified in a cell line non-permissive for viral replication, and isolating said myxoma virus sialyltransferase.

3. The method in accordance with claim 1, wherein said cultured cell line is selected from RK13 cells and CV1 cells.

4. The method in accordance with claim 1, wherein said sialyltransferase is purified chromatographically.

5. A compositions having in vitro α2,3-sialyltransferase activity and comprising a protein extract of a lysate of a eukaryotic cell culture having substantially no endogenous expression of eukaryotic α2,3-sialyltransferase, said lysate being produced in accordance with the method of claim 1.

6. Poxviral α2,3-sialyltransferase produced by chromatographic purification of the composition of claim 5, said α2,3-sialyltransferase having a sialyl motif CMP-sialic acid binding site.

7. A method for producing myxoma virus α2,3-sialyltransferase comprising harvesting viral early proteins amplified in a cell line non-permissive for viral replication, and isolating said myxoma virus sialyltransferase.

8. An isolated DNA molecule comprising the complement of nucleotides 583–1455 of the DNA sequence of SEQ ID NO:3.

9. An isolated DNA molecule comprising the complement of nucleotides 473–1345 of the DNA sequence of SEQ ID NO:10.

10. A set of degenerate primers:

CAP-I GGGATCCAT(A/T/C)TC(T/C)AG(A/G)CA(T/C)AA(A/G)CG (SEQ ID NO:1)

CAP-II GGGATCCGC(A/G)CA(T/C)AA(A/T/C/G)CC(T/G/A)ATCAT (SEQ ID NO:2).

11. An isolated α2,3-sialyltransferase comprising the amino acid sequence of SEQ ID NO:9.

12. An α2,3-sialyltransferase comprising the amino acid sequence of SEQ ID NO:13.

13. The method according to claim 1, wherein the α2,3-sialyltransferase gene is from a poxvirus from the genus Leporipoxvirus.

14. The method according to claim 13, wherein the α2,3-sialyltransferase gene is from a myxoma virus of rabbits.

15. The method according to claim 13, wherein the α2,3-sialyltransferase gene is from a poxvirus selected from the group consisting of myxoma virus Uriarra strain, myxoma virus Lausanne strain, Californian myxoma virus MSW San Francisco, Californian myxoma virus MSD San Diego, and SFV-OA shope fibroma virus original A strain.

16. The α2,3 sialyltransferase according to claim 6, wherein the α2,3-sialyltransferase is from a poxvirus from the Family Leporipoxvirus.

17. The α2,3 sialyltransferase according to claim 16, wherein the α2,3-sialyltransferase is from a myxoma virus of rabbits.

18. The α2,3 sialyltransferase according to claim 16, wherein the α2,3-sialyltransferase is from a poxvirus selected from the group consisting of myxoma virus Uriarra strain, myxoma virus Lausanne strain, Californian myxoma virus MSW San Francisco, Californian myxoma virus MSD San Diego, SFV-OA shope fibroma virus original A strain.

* * * * *